US006685618B2

(12) United States Patent
Tam et al.

(10) Patent No.: US 6,685,618 B2
(45) Date of Patent: *Feb. 3, 2004

(54) METHOD FOR DELIVERING RADIATION TO AN INTRALUMINAL SITE IN THE BODY

(75) Inventors: Lisa A. Tam, Lake Forest, CA (US); Brett A. Trauthen, Newport Beach, CA (US)

(73) Assignee: Endologix, Inc., Irvine, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 09/944,649

(22) Filed: Aug. 31, 2001

(65) Prior Publication Data

US 2003/0208096 A1 Nov. 6, 2003

Related U.S. Application Data

(60) Division of application No. 09/256,337, filed on Feb. 19, 1999, now Pat. No. 6,287,249, which is a continuation-in-part of application No. 09/025,921, filed on Feb. 19, 1998, now abandoned.

(51) Int. Cl.[7] .................................................. A61N 5/00
(52) U.S. Cl. ........................................................ 600/3
(58) Field of Search ........................... 600/1–8; 604/19, 604/53, 104, 106–107, 202; 606/194

(56) References Cited

U.S. PATENT DOCUMENTS

| 3,324,847 A | 6/1967 | Zoumboulis |
| 4,115,536 A | 9/1978 | Rothman |
| 4,124,705 A | 11/1978 | Rothman |
| 4,126,669 A | 11/1978 | Rothman |
| 4,225,790 A | 9/1980 | Parsons |
| 4,323,055 A | 4/1982 | Kubiatowicz |
| 4,423,725 A | 1/1984 | Baran |
| 4,581,017 A | 4/1986 | Sahota |
| 4,588,395 A | 5/1986 | Lemelson |
| 4,655,771 A | 4/1987 | Wallsten |
| 4,674,480 A | 6/1987 | Lemelson |
| 4,706,652 A | 11/1987 | Horowitz |
| 4,762,129 A | 8/1988 | Bonzel |
| 4,815,449 A | 3/1989 | Horowitz |
| 4,819,618 A | 4/1989 | Liprie |

(List continued on next page.)

FOREIGN PATENT DOCUMENTS

| DE | 3927001 | 2/1991 |
| EP | 0433011 B1 | 7/1994 |
| EP | 0688580 A1 | 12/1995 |
| EP | 0593136 B1 | 3/1997 |
| WO | WO 93/04735 | 3/1993 |
| WO | WO 94/23789 | 10/1994 |

(List continued on next page.)

OTHER PUBLICATIONS

Radiation Quantities and Units, ICRU Report 33, Apr. 15, 1980.
Effect of high–dose intracoronary irradiation on vasomotor function and smooth muscle histopathology, Wiedermann et al., American Physiological Society 1994.

(List continued on next page.)

*Primary Examiner*—John P. Lacyk
(74) *Attorney, Agent, or Firm*—Knobbe, Martens, Olson & Bear, LLP

(57) ABSTRACT

Disclosed is a thin film radiation source, which may be used to deliver a radioactive dose to a site in a body lumen. The source comprises a thin flexible substrate, and a layer of radioisotope attached thereto. The source may further comprise additional layers such as one or more tie layers disposed between the substrate and the radioisotope layer and one or more outer coating layers. In one embodiment, the source is wrapped around an inflatable balloon. Inflation of the balloon at a treatment site positions the source directly adjacent to the vessel wall, and allows irradiation of the site following or simultaneously with a balloon angioplasty, stent implantation, or stent sizing procedure.

25 Claims, 4 Drawing Sheets

U.S. PATENT DOCUMENTS

| | | |
|---|---|---|
| 4,878,492 A | 11/1989 | Sinofsky |
| 4,946,435 A | 8/1990 | Suthanthiran |
| 4,994,013 A | 2/1991 | Suthanthiran |
| 5,011,677 A | 4/1991 | Day |
| 5,019,369 A | 5/1991 | Presant |
| 5,040,548 A | 8/1991 | Yock |
| 5,059,166 A | 10/1991 | Fischell |
| 5,061,273 A | 10/1991 | Yock |
| 5,106,360 A | 4/1992 | Ishiwara |
| 5,152,747 A | 10/1992 | Oliver |
| 5,163,896 A | 11/1992 | Suthanthiran |
| 5,176,617 A | 1/1993 | Fischell |
| 5,199,939 A | 4/1993 | Dake |
| 5,213,561 A | 5/1993 | Weinstein |
| 5,267,960 A | 12/1993 | Hayman |
| 5,302,168 A | 4/1994 | Hess |
| 5,302,369 A | 4/1994 | Day |
| 5,342,283 A | 8/1994 | Good |
| 5,354,257 A | 10/1994 | Roubin |
| 5,411,466 A | 5/1995 | Hess |
| 5,424,288 A | 6/1995 | Order |
| 5,484,384 A | 1/1996 | Fearnot |
| 5,498,227 A | 3/1996 | Mawad |
| 5,503,613 A | 4/1996 | Weinberger |
| 5,540,659 A | 7/1996 | Teirstein |
| 5,605,530 A | 2/1997 | Fischell |
| 5,616,114 A | 4/1997 | Thornton |
| 5,618,266 A | 4/1997 | Liprie |
| 5,643,171 A | 7/1997 | Bradshaw |
| 5,653,683 A | 8/1997 | D'Andrea |
| 5,662,580 A | 9/1997 | Bradshaw |
| 5,674,177 A | 10/1997 | Hehrlein |
| 5,683,345 A | 11/1997 | Waksman |
| 5,688,220 A | 11/1997 | Verin |
| 5,707,332 A | 1/1998 | Weinberger |
| 5,713,828 A | 2/1998 | Coniglione |
| 5,720,717 A | 2/1998 | D'Andrea |
| 5,722,984 A | 3/1998 | Fischell |
| 5,728,042 A | 3/1998 | Schwager |
| 5,730,698 A | 3/1998 | Fischell |
| 5,755,690 A | 5/1998 | Saab |
| 5,762,631 A | 6/1998 | Klein |
| 5,782,740 A | 7/1998 | Schneiderman |
| 5,782,741 A | 7/1998 | Bradshaw |
| 5,782,742 A | 7/1998 | Crocker |
| 5,795,286 A | 8/1998 | Fischell |
| 5,840,008 A | 11/1998 | Klein |
| 5,840,009 A | 11/1998 | Fischell |
| 5,860,991 A | 1/1999 | Klein |
| 5,863,284 A | 1/1999 | Klein |
| 5,871,436 A | 2/1999 | Eury |
| 5,879,282 A | 3/1999 | Fischell |
| 5,911,717 A | 6/1999 | Jacobsen |
| 5,919,126 A | 7/1999 | Armini |
| 5,980,566 A | 11/1999 | Alt |
| 6,013,019 A | 1/2000 | Fischell |
| 6,019,718 A | 2/2000 | Hektner |
| 6,024,690 A | 2/2000 | Lee |
| 6,033,357 A | 3/2000 | Ciezki |
| 6,042,600 A | 3/2000 | Rosenthal |
| 6,045,495 A | 4/2000 | Weinberger |
| 6,048,299 A | 4/2000 | von Hoffmann |
| 6,050,930 A | 4/2000 | Teirstein |
| 6,059,713 A | 5/2000 | Urick |
| 6,059,714 A | 5/2000 | Armini |
| 6,059,752 A | 5/2000 | Segal |
| 6,071,227 A | 6/2000 | Popowski |
| 6,077,413 A | 6/2000 | Hafeli |
| 6,103,295 A | 8/2000 | Chan |
| 6,106,454 A | 8/2000 | Berg |
| 6,149,574 A | 11/2000 | Trauthen |
| 6,176,821 B1 | 1/2001 | Crocker |
| 6,287,249 B1 * | 9/2001 | Tam et al. ..................... 600/3 |

FOREIGN PATENT DOCUMENTS

| | | |
|---|---|---|
| WO | WO 94/26205 | 11/1994 |
| WO | WO 95/19807 | 7/1995 |
| WO | WO 95/29008 | 11/1995 |
| WO | WO 96/10436 | 4/1996 |
| WO | WO 96/13303 | 5/1996 |
| WO | WO 96/14898 | 5/1996 |
| WO | WO 96/22121 | 7/1996 |
| WO | WO 97/18012 | 5/1997 |
| WO | WO 98/33555 | 8/1998 |
| WO | WO 99/24116 | 5/1999 |
| WO | WO 99/32192 | 7/1999 |
| WO | WO 00/29501 | 5/2000 |

OTHER PUBLICATIONS

Intracoronary irradiation markedly reduces restenosis after balloon angioplasty in a porcine model, Wiedermann et al., JACC vol. 23, No. 6, May 1994.

Intracoronary irradiation markedly reduces neointimal proliferation after balloon angioplasty in swine: persistent benefit at 6–month follow–up, Wiedermann et al., JACC vol. 25, No. 6, May 1995.

Discoveries in Radiation for Restenosis, King et al., Jan. 11–12, 1996.

* cited by examiner

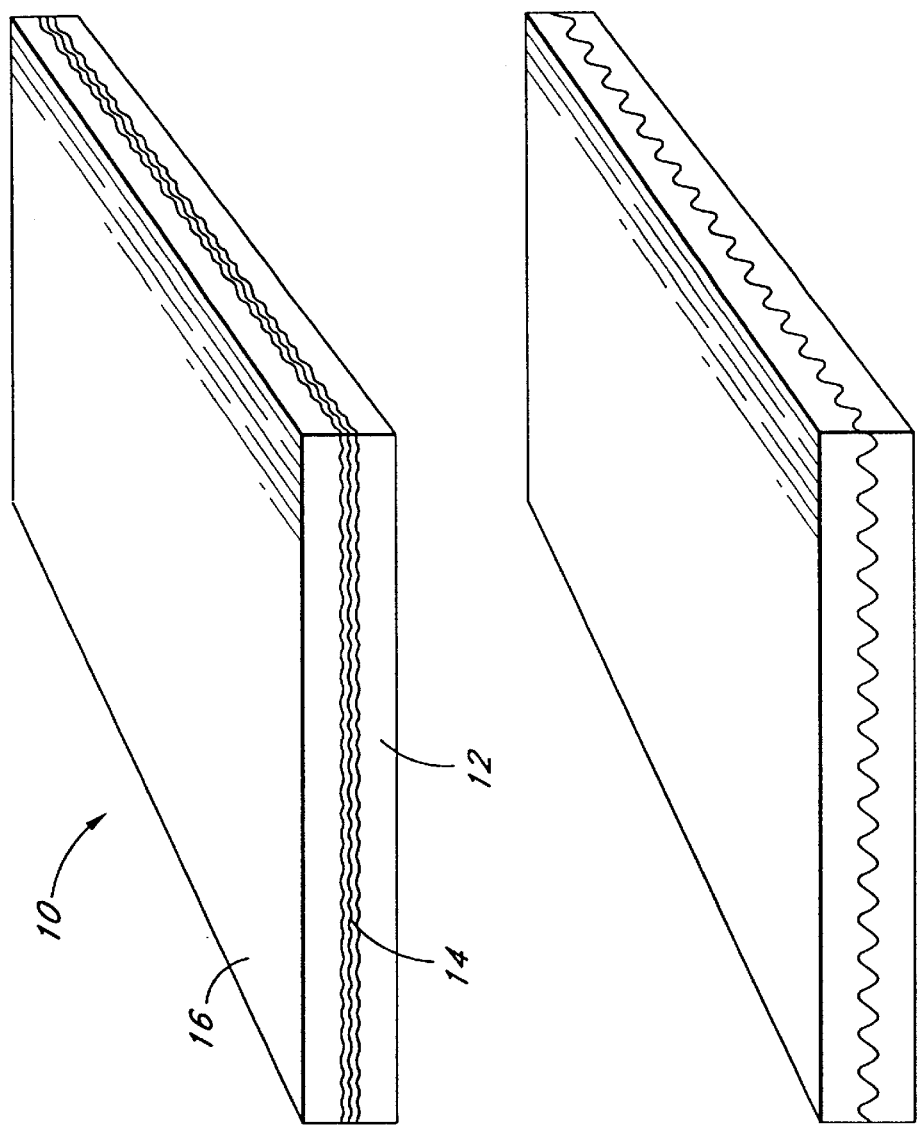

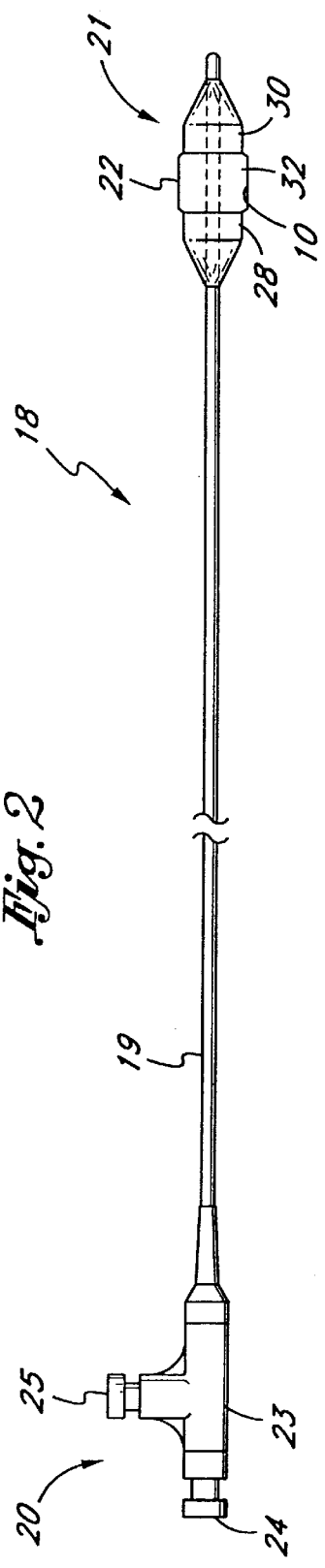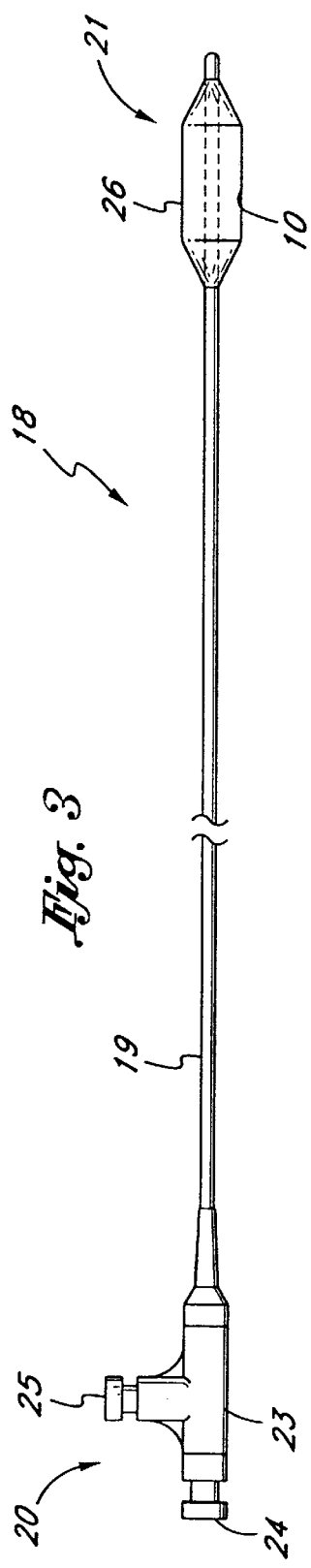

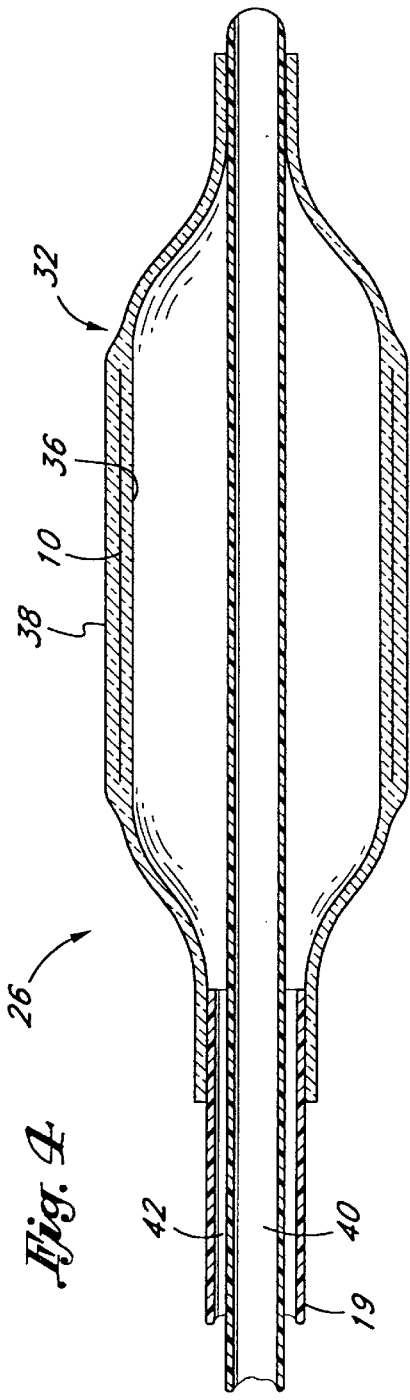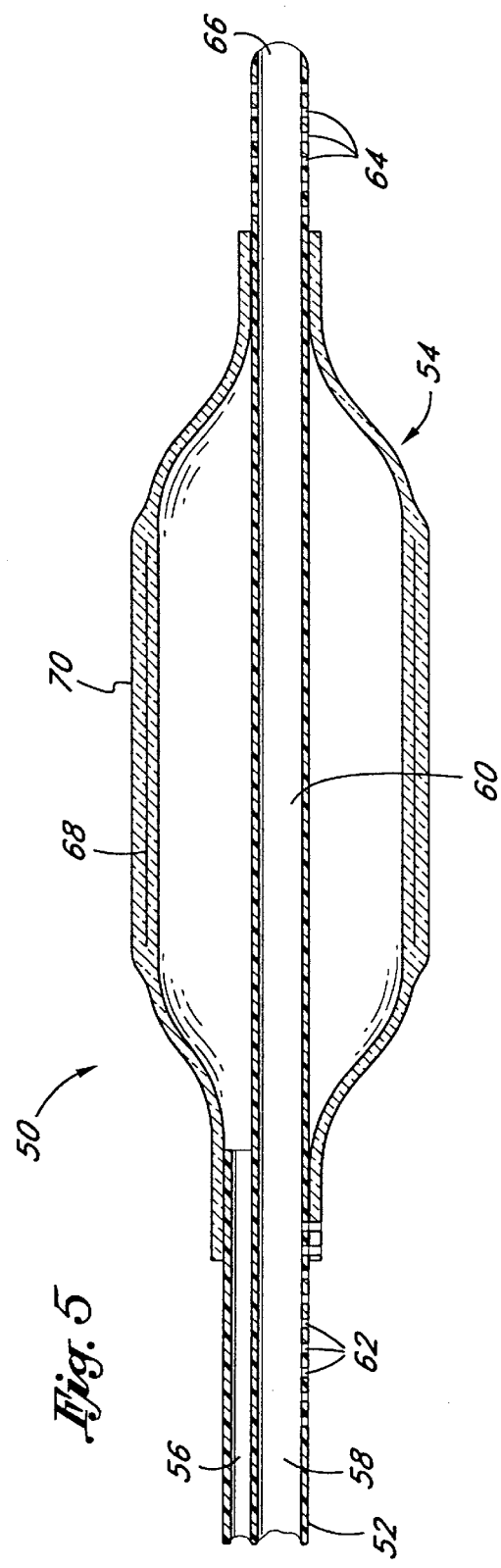

METHOD FOR DELIVERING RADIATION TO AN INTRALUMINAL SITE IN THE BODY

RELATED APPLICATION DATA

This application is a divisional application of Ser. No. 09/256,337, filed Feb. 19, 1999, now U.S. Pat. No. 6,287, 249 which is a continuation-in-part of Ser. No. 09/025,921, filed Feb. 19, 1998 now abandoned.

FIELD OF THE INVENTION

This invention relates to radiation sources which may be transported on catheters and used to deliver radiation to prevent or slow restenosis of an artery traumatized such as by percutaneous transluminal angioplasty (PTA).

BACKGROUND OF THE INVENTION

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States in 1990 and nearly one million procedures worldwide in 1997. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% or more of all patients requiring repeat PTCA procedures or by-pass surgery, with attendant high cost and added patient risk.

More recent attempts to prevent restenosis by use of drugs, mechanical devices, and other experimental procedures have had limited long term success. Stents, for example, dramatically reduce acute reclosure, and slow the clinical effects of smooth muscle cell proliferation by enlarging the minimum luminal diameter, but otherwise do nothing to prevent the proliferative response to the angioplasty induced injury.

Restenosis is now believed to occur at least in part as a result of injury to the arterial wall during the lumen opening angioplasty procedure. In some patients, the injury initiates a repair response that is characterized by hyperplastic growth of the vascular smooth muscle cells in the region traumatized by the angioplasty. Intimal hyperplasia or smooth muscle cell proliferation narrows the lumen that was opened by the angioplasty, regardless of the presence of a stent, thereby necessitating a repeat PTCA or other procedure to alleviate the restenosis.

Preliminary studies indicate that intravascular radiotherapy (IVRT) has promise in the prevention or long-term control of restenosis following angioplasty. IVRT may also be used to prevent or delay stenosis following cardiovascular graft procedures or other trauma to the vessel wall. Proper control of the radiation dosage, however, appears to be important to inhibit or arrest hyperplasia without causing excessive damage to healthy tissue. Overdosing of a section of blood vessel can cause arterial necrosis, inflammation, hemorrhaging, and other risks discussed below. Underdosing will result in inadequate inhibition of smooth muscle cell hyperplasia, or even exacerbation of hyperplasia and resulting restenosis.

The prior art contains many examples of catheter based radiation delivery systems. The simplest systems disclose seed train type sources inside closed end tubes. An example of this type of system can be found in U.S. Pat. No. 5,199,939 to Dake. In order to separate the radiation source from the catheter and allow re-use of the source, a delivery system is disclosed by U.S. Pat. No. 5,683,345 to Waksman et al. where radioactive source seeds are hydraulically driven into the lumen of a closed end catheter where they remain for the duration of the treatment, after which they are pumped back into the container. Later disclosures integrated the source wire into catheters more like the type common in interventional cardiology. In this type of device, a closed end lumen, through which is deployed a radioactive source wire, is added to a conventional catheter construction. A balloon is incorporated to help center the source wire in the lumen. It is supposed that the radioactive source wire would be delivered through the catheter with a commercial type afterloader system produced by a manufacturer such as Nucletron, BV. These types of systems are disclosed in Liprie U.S. Pat. No. 5,618,266, Weinberger U.S. Pat. No. 5,503,613, and Bradshaw U.S. Pat. No. 5,662,580.

In the systems disclosed by Dake and Waksman, the source resides in or very near the center of the catheter during treatment. However, it does not necessarily reside in the center of the artery. The systems disclosed by Weinberger and Bradshaw further include a centering mechanism, such as an inflatable balloon, to overcome this shortcoming. In either case, the source energies must be high enough to traverse the lumen of the blood vessel to get to the target tissue site in the vessel wall, thus requiring the use of higher energy sources. Higher energy sources, however, can have undesirable features. First, the likelihood of radiation inadvertently affecting untargeted tissue is higher because the absorption factor per unit tissue length is actually lower for higher energy radiation. Second, the higher energy sources are more hazardous to the medical staff and thus require additional shielding during storage and additional precaution during use. Third, the source may or may not be exactly in the center of the lumen, so the dose calculations are subject to larger error factors due to non-uniformity in the radial distance from the source surface to the target tissue. The impact of these factors is a common topic of discussion at recent medical conferences addressing Intravascular Radiation Therapy, such as the Trans Catheter Therapeutics conference, the Scripps Symposium on Radiotherapy, the Advances in Cardiovascular Radiation Therapy meeting, the American College of Cardiology meeting, and the American Heart Association Meeting.

The impact on treatment strategy is discussed in detail in a paper discussing a removable seed system similar to the ones disclosed above (Tierstein et al., Catheter based Radiotherapy to Inhibit Restenosis after Coronary Stenting, NEJM 1997; 336(24):1697–1703). Tierstein reports that Scripps Clinic physicians inspect each vessel using ultrasonography to assess the maximum and minimum distances from the source center to the target tissue. To prevent a dose hazard, they will not treat vessels where more than about a 4× differential dose factor (8–30 Gy) exists between the near vessel target and the far vessel target. Differential dose factors such as these are inevitable for a catheter in a curvilinear vessel such as an artery, and will invariably limit the use of radiation and add complexity to the procedure. Moreover, the paper describes the need to keep the source in a lead transport device called a "pig", as well as the fact that the medical staff leaves the catheterization laboratory during the treatment. Thus added complexity, time and risk is added to the procedure caused by variability of the position of the source within the delivery system and by the energy of the source itself.

In response to these dosimetry problems, several more inventions have been disclosed in an attempt to overcome the limitations of the high energy seed based systems. These systems share a common feature in that they attempt to bring the source closer to the target tissue. For example, U.S. Pat. No. 5,302,168 to Hess teaches the use of a radioactive source contained in a flexible carrier with remotely manipulated windows; Fearnot discloses a wire basket construction in U.S. Pat. No. 5,484,384 that can be introduced in a low profile state and then deployed once in place; Hess also purports to disclose a balloon with radioactive sources attached on the surface in U.S. Pat. No. 5,302,168; Hehrlein discloses a balloon catheter coated with an active isotope in WO 9622121; and Bradshaw discloses a balloon catheter adapted for use with a liquid isotope in U.S. Pat. No. 5,662,580. The purpose of all of these inventions is to place the source closer to the target tissue, thus improving the treatment characteristics.

In a non-catheter based approach, U.S. Pat. No. 5,059,166 to Fischell discloses an IVRT method that relies on a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. In addition, current stents are generally not removable without invasive procedures. The dose delivered to the blood vessel is also non-uniform because the tissue that is in contact with the individual strands of the stent receive a higher dosage than the tissue between the individual strands. This non-uniform dose distribution may be especially disadvantageous if the stent incorporates a low penetration source such as a beta emitter.

Additional problems arise when conventional methods, such as ion implantation, are used to make a radioactive source for IVRT. Hehrlein describes the use of direct ion implantation of active P-32 in his paper "Pure β-Particle-Emitting Stents Inhibit Neointima Formation in Rabbits" cited previously. While successfully providing a single mode of radiation using this method, the ion implantation process presents other limitations. For example, ion implantation is only about 10 to 30% efficient. In other words, only about one to three of every ten ions put into the accelerator is implanted on the target, and the remainder remains in the machine. Thus, the radiation level of the machine increases steadily with consistent use. With consistent use, the machine can become so radioactive that it must be shut down while the isotope decays away. Therefore, the isotope used must be of a relatively short half-life and/or the amount of radiation utilized in the process must be very small, in order to shorten the "cooling off" period. Moreover, the major portion of the isotope is lost to the process, implying increased cost to the final product.

Despite the foregoing, among many other advances in IVRT, there remains a need for an IVRT method and apparatus that delivers an easily controllable uniform dosage of radiation without the need for special devices or methods to center a radiation source in the lumen. Furthermore, a need remains for a method to make a source for IVRT which can be made without the complications and radioactive waste as seen with ion implantation methods.

SUMMARY OF THE INVENTION

There is provided in accordance with one aspect of the present invention, a radiation delivery source. The source comprises a substrate layer having at least a first side and an isotope layer on at least the first side of the substrate, wherein the isotope layer comprises a salt or oxide and at least one isotope. In one embodiment, the radiation delivery source further comprises an outer coating layer. The coating layer may comprise any of a variety of materials such as cyanoacrylates, acrylics, acrylates, ethylene methyl acrylate/ acrylic acid, urethanes, polyvinylidene chloride, polybutylvinyl chloride, other polymers or combinations thereof. The outer coating layer may also comprise biocompatible materials such as heparin.

Preferably, the isotope in the isotope layer is selected from the group of gamma emitters with energies less than about 300 keV including I-125, Pd-103, As-73, and Gd-153, or the high energy beta group ($E_{max}>1.5$ meV) including P-32, Y-90 and W/Re-188. Other isotopes not currently mentioned, can be utilized by the invention described herein. The selection of these isotopes, however, allows the source to be shielded in a material such as leaded acrylic in commercially available thickness of 15–30 mm, or in a lead tube of approximately 0.3–0.5 mm wall thickness. Some of the other isotopes which may be deemed suitable for use in the present invention or for a particular intended use, include Au-198, Ir-192, Co-60, Co-58, Ru-106, Rh-106, Cu-64, Ga-67, Fe-59, and Sr-90. The selection of an isotope may be influenced by its chemical and radiation properties.

In another aspect of the present invention, a radiation delivery source is provided having a substrate layer, a tie layer bound thereto, and an isotope layer bound to the tie layer. The tie layer comprises one or more materials selected from the group consisting of metals, metal salts, metal oxides, salts, alloys, polyester, polyimide, and other polymeric materials. The isotope layer comprises a relatively insoluble metal salt or oxide, and at least one isotope. In one embodiment, the source further comprises an outer coating layer.

In one embodiment, the substrate layer is a thin film layer, which may be attached to or which comprises at least a portion of an inflatable balloon.

In accordance with another aspect of the present invention, there is provided a method for making a radiation delivery source. The method comprises the steps of providing a substrate and coating the substrate with an isotope layer comprising a relatively insoluble salt of at least one isotope. In one embodiment, the coating step comprises the steps of coating the substrate with at least one layer of metal, reacting the layer of metal to form a metal oxide or metal salt, and exposing (e.g., dipping) the layer of metal oxide or metal salt to a solution comprising a plurality of isotope ions to form the isotope layer. In another embodiment, the coating step comprises the steps of coating the substrate with a layer of metal salt or metal oxide, exposing the layer of metal salt or metal oxide to a fluid comprising a plurality of isotope ions to form the isotope layer. In one embodiment, the method further comprises the step of coating the isotope layer with a coating layer.

In accordance with a further aspect of the present invention, there is provided a radiation delivery balloon catheter. The balloon catheter comprises an elongate flexible tubular body, having a proximal end and a distal end. An inflatable balloon is provided on the tubular body near the distal end thereof. The balloon is in fluid communication with an inflation lumen extending axially through the tubular body.

A thin film radiation source is provided on the balloon, said thin film source comprising a substrate and an isotope layer. In one embodiment, a tie layer is provided between the substrate and the isotope layer. In another embodiment, a coating layer is provided over the isotope layer. The substrate may comprise a portion of the wall of the balloon, or a separate substrate layer attached to the surface of the balloon. This isotope layer may be bound directly to, or impregnated within, the wall of the balloon. In one embodiment, a tubular outer sleeve is provided for surrounding the thin film radiation source and securing the radiation source to the balloon.

In another embodiment, the radiation delivery balloon catheter is provided with a proximal guidewire access port on the tubular body, positioned substantially distally of the proximal end of the tubular body, for providing rapid exchange capabilities. In addition to, or instead of the rapid exchange feature, the catheter may be provided with at least one proximal perfusion port on a proximal side of the balloon in fluid communication with at least one distal perfusion port on a distal side of the balloon, for permitting perfusion of blood across the balloon while the balloon is inflated at a treatment site.

In accordance with a further aspect of the present invention, there is provided a method of treating a site within a vessel. The method comprises the steps of identifying a site in a vessel to be treated, and providing a radiation delivery catheter having an expandable balloon with a thin film radiation delivery layer thereon. The radiation delivery layer preferably has a substrate layer and an isotope layer. The balloon is positioned within a treatment site, and inflated to position the radiation delivery layer adjacent the vessel wall. A circumferentially substantially uniform dose of radiation is delivered from the delivery balloon to the vessel wall. The balloon is thereafter deflated and removed from the treatment site.

In one embodiment, the method further comprises the steps of positioning a stent on the balloon prior to the positioning step, and expanding the stent at the treatment site to implant the stent.

In accordance with a further aspect of the present invention, the site identification step in the foregoing method comprises identifying a site having an implanted stent or graft. The balloon is positioned within the previously implanted stent or graft and expanded to deliver a radiation dose within the previously implanted stent or graft. The balloon may either be inflated to a relatively low inflation pressure, to bring the radiation source into contact with the interior wall of the stent or graft without further stent or graft expansion, or inflated to a relatively higher inflation pressure, to further expand the stent or graft while delivering a radiation dose.

In accordance with a further aspect of the present invention, there is provided a method of simultaneously performing balloon dilatation of a stenosis in a body lumen, and delivering radiation to the body lumen. The method comprises the steps of identifying a stenosis in a body lumen, and providing a treatment catheter having an elongate flexible tubular body with an inflation balloon near a distal end thereof, and a cylindrical thin film radiation delivery layer on the balloon. The balloon is percutaneously inserted and transluminally advanced through the body lumen, and positioned within the stenosis. The balloon is thereafter inflated to radially expand the vessel in the area of the stenosis, and simultaneously deliver radiation from the thin film to the vessel wall.

In accordance with another aspect of the present invention, there is provided a method of simultaneously performing a balloon dilatation of a stenosis in a body lumen, delivering a stent, and delivering radiation to the body lumen. The method comprises the steps of identifying a stenosis in a body lumen, and providing a treatment catheter having an elongate flexible tubular body with an inflation balloon near a distal end thereof, and a cylindrical thin film radiation delivery layer on the balloon. The balloon is percutaneously inserted and transluminally advanced through the body lumen, and positioned within the stenosis. The balloon is thereafter inflated to radially expand the vessel in the area of the stenosis, expand and deliver the stent and simultaneously deliver radiation from the thin film to the vessel wall.

In accordance with a further aspect of the present invention, there is provided a method of producing a radiation delivery catheter having a target activity. The method comprises the steps of providing a catheter dimensioned for insertion within a body lumen, and providing a thin film radiation source having a known radioactive activity per unit length. A sufficient length of the radiation source is wrapped around the catheter to produce a net radioactive activity of at least about the target activity. Preferably, the catheter is provided with a balloon, and the thin film radiation source is wrapped around the balloon. In one embodiment, the method further comprises the step of providing a protective tubular sheath around the radiation source, to secure the source to the catheter.

Further features and advantages of the present invention will become apparent to those of skill in the art in view of the detailed description of preferred embodiments which follow, when considered together with the attached drawings and claims.

BRIEF DESCRIPTION OF THE DRAWINGS

FIG. 1 is a schematic perspective view of a thin film radiation source in accordance with the present invention.

FIG. 1A is a schematic perspective view of an alternate thin film source in accordance with the present invention.

FIG. 2 is a schematic side elevational view of a catheter incorporating the thin film source of the present invention.

FIG. 3 is a schematic side elevational view of an alternate catheter incorporating the thin film source of the present invention.

FIG. 4 is an enlarged side elevational cross-sectional view through a balloon incorporating the thin film source of the present invention.

FIG. 5 is an enlarged elevational cross-sectional view of a balloon incorporating the thin film source in accordance with another aspect of the present invention.

Figure 1B:
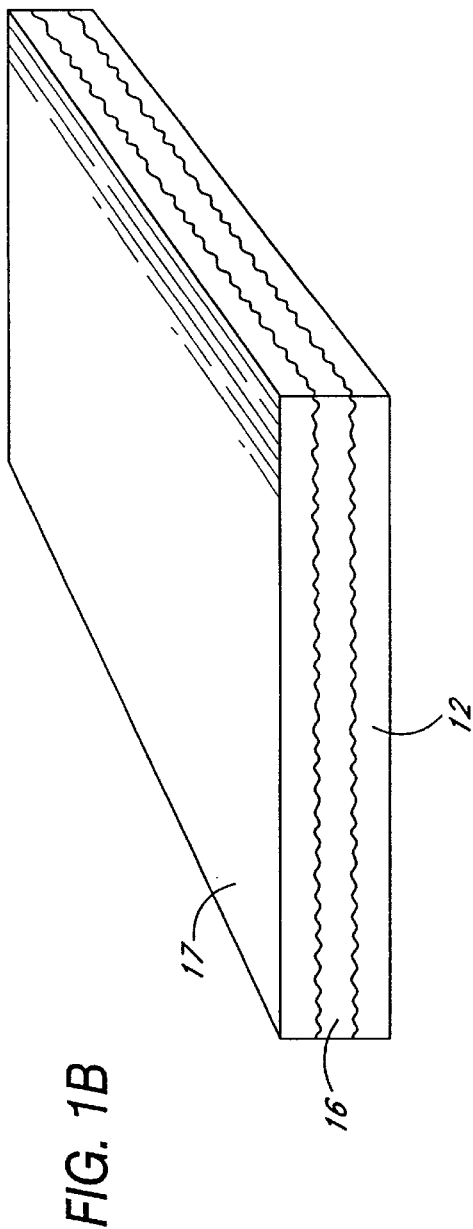
FIG. 1B is a schematic of a cross-section of one embodiment of the radiation delivery source of the present invention having a substrate layer, an isotope layer and a coating layer.

The drawing figures are not necessarily to scale.

DETAILED DESCRIPTION OF THE PREFERRED EMBODIMENT

This invention provides a novel source design, new in terms of structure, materials and production methods. The invention can be generally described as a thin film radioactive source intended for site specific delivery of radiation ("brachytherapy") to an anatomical structure. As presently contemplated, one embodiment of the source design is intended for incorporation into the balloon segment of a vascular dilatation catheter such as that disclosed in U.S. Pat. No. 5,782,742, Crocker, et al., the disclosure of which is incorporated in its entirety herein by reference.

Alternatively, the source could be incorporated into traditional "seeds," or placed on a wire, or on a trocar, or most any other delivery system. The thin film can be rolled up into a cylindrical configuration for insertion and unrolled in-situ for positioning adjacent the vessel wall either by itself or as a laminate on a flexible metal or polymeric support sheet, such as disclosed in U.S. patent application Ser. No. 08/965, 900, entitled Radiation Delivery Catheter, filed Nov. 7, 1997 by von Hoffmann, the disclosure of which is incorporated in its entirety herein by reference. However, for the sake of simplicity, the present invention will be described herein primarily in the context of a balloon structure for use in intravascular procedures.

The term "thin film source" is descriptive of the invention's structure. Referring to FIG. 1, the source 10 comprises of a thin sheet, or "substrate" layer 12, a chemical attachment or "tie" layer 14 for binding the isotope, and an isotope species 16. The substrate 12 can consist of a very thin (1–20 microns, or from about 0.00004 to about 0.0008" thickness) sheet or tubing. At these thicknesses, a wide variety of biologically compatible materials are very flexible and conforming. Examples of substrates commercially available at these thicknesses are Mylar® (polyester), Kapton® (polyimide), and polyethylene terephthalate (PET) sheet or tubing, or even metal foils.

Figure 1C:
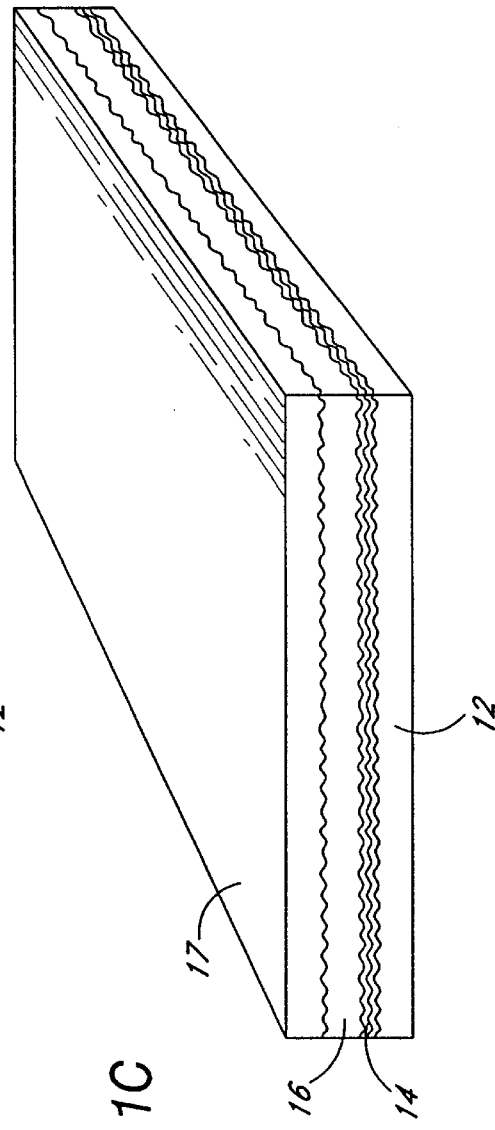
FIG. 1C is a schematic of a cross-section of one embodiment of the radiation delivery source of the present invention having a substrate layer, a tie layer, an isotope layer and a coating layer.

FIGS. 1A–1C show additional embodiments of the thin film source of the present invention. Referring to FIG. 1A, a schematic of a cross-section of a two-layer embodiment of thin film source is shown. The first or innermost layer is the substrate 12, and the second or outer layer is the isotope layer 16.

Referring to FIG. 1B, a schematic of a cross-section of thin film source, wherein the source has three layers, is shown. The first or innermost layer is the substrate 12, the second or middle layer is the isotope layer 16, and the outer layer is the coating layer 17.

Referring to FIG. 1C, a schematic of a cross-section of a four-layer embodiment of the thin film source of the present invention is shown. The four layers are the substrate layer 12, tie layer 14, isotope layer 16, and coating layer 17.

The thin film sources of the present invention are comprised of two or more layers of materials. There may or may not be a clear visual or physical distinction between the various layers in the source 10 because each layer need not be a discrete structural element of the thin film source 10. As the layers bond together to form the source, they may become blended, alloyed, intermingled or the like to form what looks and acts like a single layer having a somewhat heterogeneous composition. For this reason, the various layers as defined and used herein are intended to denote the functional characteristics of the components or help denote what process steps are used in their formation, whether through the use of discrete structural layers or layers blended with neighboring layers, the selection of which will be apparent to those of skill in the art in view of the particular materials and components used.

For example, the term tie layer as used herein is intended to denote a functional characteristic which enables securing of the isotope species 16 to the substrate 12, whether through the use of a discrete structural layer (such as an adhesive or functionally analogous component) or a surface modification to the substrate 12 (such as chemical activation), the selection of which will be apparent to those of skill in the art in view of a particular substrate 12 material and isotope layer 16 material. For example, FIG. 1A schematically represents a substrate 12 having an isotope zone 16 comprising at least one isotope.

The thin film sources of the present invention all comprise a substrate layer or substrate 12. The thickness and composition of the substrate layer 12 can be varied widely, depending upon the catheter design or the design of the other medical device to which the isotope species 16 is to be bound. For example, materials in the thickness of conventional PTCA balloons (from about 0.0005 to about 0.005 inches) may be utilized, such as where the balloon itself is used as the substrate 12. A balloon substrate may be either of the compliant or non-compliant variety, as known in the art. In addition, substantially thicker substrates can be utilized where structural support is desirable as will be apparent by those of skill in the art in view of the disclosure herein. The sustrate 12 may be polymeric or a metal, depending upon the desired characteristics of the finished product.

The shape of the source is generally dictated by the geometry of the substrate 12. When present, any of the layers described herein, other than the substrate, are disposed over at least one surface of the source, and may be disposed over the entire surface of the source. All layers present in a given embodiment need not cover the same areas of the substrate or the entire surface of the source. In one embodiment, the tie layer and isotope layer cover only a portion of the substrate, and the entire substrate is coated with one or more coating layers.

The thin film sources also all comprise an isotope layer 16. The isotope layer comprises at least one radioactive isotope. Such isotopes are preferably either beta- or gamma-emitting. The composition of the isotope layer may be of a wide variety of possibilities. In one embodiment, the isotope layer comprises a collection of individual isotope ions, atoms, or compounds attached to the layer below, preferably in a relatively even distribution. In another embodiment, the isotope layer comprises a metal salt wherein same or all of one ion of the salt has been replaced by isotope ions (simple or complex). Such a salt-containing isotope layer may be bound directly to the substrate layer 12 or to a tie layer 14, if present. The isotope layer preferably has an isotope density or nuclide density in the range of $10^{10}$–$10^{25}$ atoms/$cm^2$, more preferably about $10^{13}$ –$10^{15}$ atoms/$cm^2$ more preferably about $10^{14}$ atoms/$cm^2$ and has a thickness of preferably 100–10,000 Angstroms thick, more preferably about 500–1500 Angstroms thick.

As used herein, the term "metal salt" refers to a compound comprised of at least one anion and at least one cation. The anions and cations of the metal salt may be either simple (monatomic) ions such as $Al^{3+}$, $Cl^-$, $Ca^{2+}$, and $Ag^+$, or complex (polyatomic) ions such as $PO_4^{3-}$ and $WO_4^{2-}$. At least one of the ions in the metal salt should comprise a metal. The term "metal" as used herein means all metals, including, for example, semimetals, alkali metals, and alkaline earth metals. Preferably metals are selected from the transition metals or main group of the Periodic Table of the Elements. The term "metal salt" as used herein in its broadest sense can encompass metal oxides.

The thin film sources of the present invention may further comprise at least one tie layer 14. The tie layer 14 lies between the substrate 12 and isotope layer 16 and may act to increase the tenacity of attachment of the isotope layer 16 to the substrate 12. The tie layer 14 may be any composition or structure which functions to bind the isotope 16 to the substrate 12. The tie layer 14 may comprise adhesives, chemically activated surfaces, mechanical locking structures, a chemical coating layer, or a layer of one or more an organic or inorganic compound. Preferred tie layer materials include metals, alloys, metal salts, alumina and other metal oxides, polyester, polyimide and other polymers. Its chemical composition and structure can be varied, depending on the isotope to be attached. It can be an organic or inorganic material or compound; it must only have the appropriate chemistry to attract and bind the isotope or isotope layer materials. The tie layer may be applied to one or both surfaces of the substrate, depending on factors such as the desired activity, composition or geometry of the finished product. In one embodiment, the tie layer 14 is a layer of metal or metal oxide, and it is 100 to 10,000 Angstroms thick, more preferably 200 to 500 Angstroms thick.

The thin film sources of the present invention may further comprise one or more coating layers 17. A coating layer 17, can act as a sealing means to protect the isotope layer from mechanical abrasion or other injury which could remove radioisotopes from the isotope layer and thus reduce its activity. Although the isotopes in the sources of the present invention may be sufficiently adherent without the addition of a coating layer, addition of a coating layer may aid in providing sufficient protection for the device to be classified as a sealed radiation source, i.e. one that has less than 5 nCi of removable activity. The coating layer may also provide the additional advantage of sealing or binding the layers of the source together.

The coating may be a metal or plastic. Plastic coating materials are preferably biocompatible, but not excessively biodegradable. Preferred materials include cyanoacrylates, acrylics, ethylene methyl acrylate, ethylene methyl acrylate/acrylic acid (EMA/AA), urethanes, thermal plastic urethane (TPU) polybutyl vinyl chloride (PBDC), polyvinylidene chloride (PVDC, such as Saran® polyethylene, polyethylene terephthalate, nylon and the like. Likewise, metal coatings can be used as well. If the coating is metal, the metal used is preferably one which is bio-stable. For example, platinum, gold, or titanium may be vapor deposited on the surface to encapsulate the isotope layer.

The foregoing thin film structures offer several advantages over existing source designs. First, the source can conform to almost any shape, unlike conventional seed or solid wire type sources or even a thin metal film. Thus, this type of source is ideal for incorporation into flexible catheter-like delivery systems.

Secondarily the sheet can be wrapped several times around itself without substantially stiffening the source 10. For example, the thickness of a typical polyethylene balloon used in angioplasty is at least about 0.0015". For an eight micron Mylar sheet, this corresponds to 5 wraps to achieve equivalent thickness. The importance of this feature is that the activity of the source can be readily manipulated by the number of layers of the thin film 10 used to form the final source. Because the activity of the source is proportional to the number of isotope atoms on the substrate, larger surface areas will have higher atom counts than smaller ones. Thus, the total source activity will be proportional to the surface area of the substrate.

The ability to increase the activity of the source by wrapping it without a material increase in the size of the device is also important because it broadens the number of isotopes that can be used for this application. This is because radioisotopes are different in their specific activity, which is the amount of radioactivity per unit isotope mass (Curies/gram). Thus the thin film source 10 of the present invention can enable the use of an isotope with low specific activity but otherwise desirable properties. An example of this is the use of tungsten/rhenium-188 (W/Re-188). This species generates a beta particle with similar properties to Sr/Y-90, but without the disposal problems and health risks associated with the long half life (28.5 years) and bone destruction associated with Sr/Y-90. The issue limiting W/Re-188 is that it has a lower specific activity than Sr/Y-90, and so is more difficult to achieve adequate activity levels in a small volume. This may be overcome using a sufficient surface area of the thin film source 10 of the present invention configured as a series of concentric wrappings such as around a balloon.

The activity of delivery devices which include the thin film source 10 of the present invention can be thus increased in a variety of ways depending upon the nature of the delivery device to which the source is affixed. For example, in the context of a thin film wrapped around or incorporated into the surface of a continuous circumferential support such as a balloon, the thin film may be wrapped around the balloon anywhere from about one full revolution through about 10 or 20 or more revolutions depending upon the desired activity level, and required flexibility and collapsed profile characteristics of the balloon.

In general, for a gamma radiation source the activity of adjacent layers will be additive, whereas the net activity for a wrapped beta source may be something less than a straight multiple of the number of layers of radioactive thin film. In many applications, from about 2 to about 20 layers will be utilized, and, generally, no more than about 6 or 8 layers will be utilized for manufacturing reasons and in order to maintain high catheter flexibility. Optimization of the number of layers of thin film in the context of a particular delivery structure, isotope and required characteristics can be determined through routine experimentation by one of skill in the art in view of the disclosure herein. For example, isotope uptake into the substrate can be varied to yield a desired total activity/area, monitored by standard dosimetry measurements, using radiochromic film or water phantoms, as described in National Institute of Standards & Technology publication (NIST, Soares, et al., Washington, D.C. 1997).

Alternatively, the thin film can be layered in the form of a multilayer stack, when used on a delivery structure which does not have a continuous circumferential surface. Thin film stacks may be useful, for example, in connection with seeds, wires, or a thin metal or plastic support of the type disclosed in Ser. No. 08/965,900 to von Hoffmann.

A further advantage of the thin film configuration of the present invention is that the substrate surface area can be increased by drilling or etching micro holes in the film. As long as the diameter "d" of the holes meets the condition d<2t, where "t" is the thickness of the substrate 12, the surface area will increase by the factor (2t/d−1) per hole. Microporous materials are available commercially with whole diameters in the range of from about 0.2 microns to about 5 microns or more. Thus, this technique is yet another way in which achievable activities of the source can be increased by increasing available surface area of the substrate, while at the same time maintaining flexibility and small size.

Activity and lifetime of sources can, in part, be manipulated by the choice of isotope. The relatively rapid time of decay and concomitant loss of "strength" of short half-life isotopes may present product problems, such as lack of consistent dosing, in addition to manufacturing problems. Take for example, P-32 implanted on three sources at the same time to a level of 10 μCi using the method described in the above-cited paper by Hehrlein (*Circulation,* 1996). Assume all sources are prepared and available for use on day 0. If the first is used immediately, the second after 7.1 days (one half of a half-life), and the third after 14.3 days (one half-life), then the available dose, as compared to the first source, is much less for the second and third sources. To achieve a particular dose, a weaker source must be left at the treatment site for a longer time than a stronger source. Thus, the required indwell time for a set of catheter-based sources would vary, such that one used 14 days later would need to be left at the treatment site twice as long as a source used on day 0.

Some of the difficulties associated with a lack of consistent dosing which can result with short half-life isotopes, as discussed above, could be overcome through the use of longer half-life isotopes. If, instead, sources were implanted with an isotope having a 60-day half-life, the dose variation between maximum and minimum over the fourteen-day time frame would be reduced to 15%, and over a 7-day period to just 8%. The total dose supplied to the tissue by the longer half-life isotope will be greater. Effective dose and dose rate, however, remain to be determined. It is generally known that radiation dose can be increased if it is fractionated or given over extended periods. Only experimentation can answer the questions of dose and dose rate. However, if a long half-life isotope eventually proves effective, the lowest amount of radiation required to perform treatment is always preferable to any higher amount for safety reasons.

The radioisotopes used in the thin film sources of the present invention may be beta or gamma emitters, or both, and may have any of a wide range of half-lives, both long and short. The particular isotope, or combination of isotopes as well as the concentration of isotopes in the source (which determines the dose), can be chosen by one skilled in the art to serve the needs of a particular application. In a recent paper presented by Howard Amols at the January 1998 Scripps Clinic Conference on Intravascular Radiation Therapy entitled "Choosing the Right Isotope: What's New? Insights into Isotopes or Why Is it so Hard to Find the Ideal Isotope?," the author states that the best isotope choice from the perspective of both physics and dosimetry would be a photon source with an energy greater than 3 MeV and a half-life greater than 7 days. Shirish K. Jani, in a lecture entitled "Does the Perfect Isotope Exist?" at the same conference states that the perfect isotope for vascular brachytherapy would exhibit a low dose gradient, low dose levels to surrounding body tissues, manageable radiation exposure levels around the patient and a long half-life. Iodine-125 (I-125, half-life 60 days) and tungsten-188/rhenium-188 (W/Re-188, half-life 70 days) are candidates to meet these criteria, and also have long half-lives. Thus, these are two preferred radioisotopes for use in the present invention.

Preferred radioisotopes are selected from the group of gamma emitters (or x-ray emitters) with energies less than about 300 KeV such as I-125, Pd-103, As-73, Gd-153, or the high-energy beta emitters ($E_{max}$>1.5 meV) including P-32 and W/Re-188, or others as may be deemed suitable for a particular use. The selection of the isotope may be influenced by its chemical and radiation properties, and other isotopes not mentioned herein, but which have properties suitable for a particular application, can be utilized in the present invention. Preferred radioisotopes used in the thin film sources of the present invention may be purchased from Oak Ridge National Laboratory (Oak Ridge, Tenn.), New England Nuclear (NEN) or any other commercial suppliers of radioisotopes.

For all of the attachment systems of the present invention, the number of atoms of a particular isotope required on the substrate to achieve a desired activity level is readily calculated. The desired total activity is multiplied by Avogadro's number, and then the result is divided by the product of Specific Activity and the atomic weight of the isotope. The number of isotope atoms per unit substrate area or Nuclide Density, is then calculated by dividing again by the total source surface area. The corresponding activity density is calculated by dividing the total activity by the substrate surface area. By way of example, P-32, with an atomic weight of 32 grams/mole, a specific activity of $2.857 \times 10^5$ Ci/g (Brown & Firestone, Table of Radioactive Isotopes, Wiley, 1986), Avogadro's number $6.02 \times 10^{23}$ atoms/mole, and a thin film substrate layer of measuring 2.1 cm width by 0.94×N cm length, where N is the number of wraps of the source. Dimensions such as this would be appropriate for covering a 3 mm diameter×3 cm length balloon as described elsewhere herein with N wraps. In this case, the substrate surface area is approximately 2 cm$^2$ per side, or 4 cm$^2$ total per wrap. Estimating the desired activity of the source at 200 mCi, the number of isotope ions and resulting nuclide and activity densities can be calculated as follows:

Ion And Activity Density Calculations
P-32, 200 mCi Total Activity, Two Coated Sides

| Number of Wraps | Total Area cm$^2$ | Nuclide Density Atoms/cm$^2$ | Activity Density Ci/cm$^2$ |
|---|---|---|---|
| 1 | 4 | $6.59 \times 10^{15}$ | 0.50 |
| 2 | 8 | $1.65 \times 10^{15}$ | 0.25 |
| 3 | 12 | $1.1 \times 10^{15}$ | .016 |
| 5 | 20 | $6.59 \times 10^{14}$ | .010 |
| 8 | 32 | $4.12 \times 10^{14}$ | .0063 |

Note that for P-32, a nuclide density of $6.59 \times 10^{15}$ atoms/cm$^2$ is equivalent to $3.2 \times 10^{-6}$ g, or 3.2 micrograms, of that material. This mass of isotope is readily incorporated onto the substrates using any of the chemical attachment or direct deposition methods described herein.

As shown by the table, the ability to multiply the number of layers opens many options to the design of the source. If a high number of atoms can be attached with a given process, then the number of wraps can be lower. If a process yields a lower activity density but is very cost effective, more wraps can be used to compensate for the lower activity density. This feature is important to the designer because the range of achievable activity for the source determines treatment time, product shelf life, and the range of isotope options practical for the application.

The ion implantation process of P-32 can serve as an example of these principles in a practical setting. Commercial ion implantation machines can readily achieve $10^{17}$ ions/cm$^2$ on a thin sheet substrate, such as polyimide described in this document. This density level would appear to provide more than enough activity on a single wrap for a pure isotope. However, pure isotopes are not readily available and are extremely expensive to manufacture. Those skilled in the art of nuclear physics will know that P-32, by way of example, can be made from P-31 in a nuclear reactor by neutron bombardment in a process known as an (n,γ)

reaction, or it can be made from Sulfur-32 (S-32) in an accelerator in a process known as a (n,p) reaction. The processes differ widely in cost and resulting isotope purity. The reactor process is relatively inexpensive, but may yield only about 0.1–0.01% P-32 to P-31; the accelerator process is more expensive by a factor of 10–100, but the isotope purity can be very high, on the order of 99%. The thin sheet substrate thus allows the designer the flexibility to optimize between source purity and cost while achieving similar activity level. This in turn allows flexibility toward the activity of the finished source, which effects treatment time and shelf life. The same applies to the other isotope attachment methods discussed herein, and holds true regardless of the radiation type (gamma or beta) or energy level.

In accordance with one isotope attachment technique, a thin film substrate is treated with a tie layer composed of a three-dimensional matrix with an ionic compound. The choice of the ionic compound is made to encourage the ion desired to bond within the tie layer. In one embodiment, the three-dimensional matrix is polyvinyl pyrrolidone (PVP) with an ionic compound containing a Br anion. The PVP matrix is commonly used in hydrophilic coatings and as a carrier for $I_2$ in antimicrobial applications. The three-dimensional matrix is designed to hold and increase the concentration of ionic compound on the surface. Direct attachment of the ionic compound would result in layers on the molecular scale. To accomplish attachment, the treated substrate is placed in an ionic solution of I-125 ($Na^{125}I$, a commercially available form of I-125). I-125 anions exchange with Br anions from the PVP, thus incorporating I-125 into the tie layer and producing a gamma radiation source. This system can work alternatively in a solution comprising $^{32}P$-containing ions such as $H_3^{32}PO_4$ (a commercially available form of P-32) to form a beta emitting source.

In one specific embodiment of the present invention, a generally rectangular polyester sheet having a width of about 2 cm, a length of about 3 cm and a thickness of about 12 microns was coated with a PVP ion exchange surface and soaked in a 0.125 wt % I-125 in NaI solution. The resulting source was thereafter wrapped around a balloon having an inflated diameter of about 3.0 mm and an axial length of about 30 mm. The sheet length of 3 cm allowed the source to be wrapped around the inflated balloon approximately 3 full revolutions. Thus, in this context, sheet length corresponds to the circumferential direction as wrapped around the balloon, and sheet width corresponds to the axial length of the source along the balloon. In this embodiment, the activity of the source was approximately 110 milliCuries per centimeter length of the substrate sheet. Thus, by providing three full revolutions, a net activity of about 330 milliCuries was produced, an activity similar to that disclosed by Teirstein for the Ir-192 (gamma) source used in the Scripps study. Using the present invention, the net activity could conveniently be doubled, for example, by lengthening the substrate sheet to about 6 cm, thereby enabling six revolutions of the substrate around the balloon. This may accomplish a respective reduction in treatment time of 50%.

In cases where adequate activity can be achieved with a single wrap of the source, a thin tube could be used alternatively to the sheet. For example, PET tubing can be commercially obtained with wall thicknesses similar to the sheet material described earlier (0.0003–0.001 inch). The tube construction may allow for simpler assembly, but otherwise it possesses the same properties as the rolled sheet.

There are alternative ways of taking advantage of the thin film structural properties, however, without utilizing a chemical attachment system for the isotopes. For example, the radioactive isotope or a salt thereof can be attached directly to the sheet without a distinct tie layer 14 through ion implantation, vapor deposition, or sputtering. Thus, for some techniques, a distinct tie layer 14 is omitted completely. See FIGS. 1A and 1B.

Other methods of direct isotope attachment to the substrate can be considered for metal isotopes. For example, vapor deposition and sputtering can be used to deposit metal isotopes on the substrate. The layers in these processes can be controlled to submicron thicknesses, such that all of the physical/mechanical advantages described in the above paragraphs for chemical attachment systems are maintained: flexibility, ability to adjust activity based on multiple wraps, ability to utilize less active isotopes.

Preferred methods of making the isotope layer of the present invention may begin with either a substrate to be coated or a tie layer to serve as the place of attachment. Preferred methods comprise exposing surfaces to fluids comprising reactants or isotopes.

Such fluids may be gaseous (including plasma and vapor) or liquid (such as solutions), with liquid solutions being preferred. As such, the methods below are described in terms of liquid solutions.

Some preferred methods of making the isotope layer of thin film sources of the present invention comprise, in part, either one or both of the following solution processes: (1) oxidation in an acidic solution to form a metal salt from a metal; and (2) ion exchange wherein ions at or near the surface of the metal salt are exchanged with those present in a solution. The first process is based on differences in oxidation-reduction potentials, and the second process is based on differences in solubility. These processes will be taken in turn.

In the first process, the equilibrium is driven by principles of oxidation-reduction (redox). A metal, in the form of a pure metal or part of an alloy, may be converted to a metal salt when it is placed in solution comprising an oxidizing agent. Many metals, including those in preferred embodiments discussed below, can be readily oxidized in solution to form metal cations, which may then form salts with anions in solution.

Whether or not a particular reaction of an oxidizing agent and a metal will occur spontaneously can be predicted by reference to a standard table of half-cell potentials such as that in *CRC Handbook of Chemistry and Physics*, (CRC Press). If the sum of the potentials of the oxidation half-reaction and the reduction half-reaction is positive, then the reaction will occur spontaneously.

For example, it can be predicted that when silver is added to an acid solution of sodium chlorite, the silver will be oxidized. When added to the solution, sodium chlorite ($NaClO_2$) disproportionates to form hypochlorous acid and chlorine dioxide, which is capable of oxidizing silver as shown below:

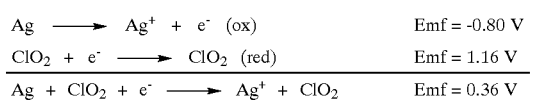

In addition to the reaction shown above, the hypochlorous acid undergoes a redox reaction whereby chloride ions are produced, which then couple with the silver cations to form silver chloride.

The second process is a solubility-driven ion exchange. When, for example, two anions are placed in solution with a given cation, there is a driving force which results in the formation of the metal salt which is less soluble/more insoluble. Because it is difficult to compare solubilities and thus predict behavior when the relative terms "soluble" and "insoluble" are used, solubility is related to a type of equilibrium constant, the solubility product ($K_{sp}$), in order to quantify the degree of solubility for a given compound. The solubility product is equal to the concentrations of the dissociated ions of the salt at equilibrium, that is for salt AB, $K_{sp}=[A^+][B^-]$ wherein $[A^+]$ and $[B^-]$ are the concentrations of the A cation and the B anion, respectively. If a salt is fairly soluble, the concentrations of its component ions in solution will be relatively high, leading to a relatively large $K_{sp}$. On the other hand, if a salt is fairly insoluble, most of it will be in solid form, leading to low concentrations of the ions and a relatively small $K_{sp}$. Thus, when comparing two salts of the same metal, the salt with the lower $K_{sp}$ is the more insoluble of the two. Solubility products for most common compounds can be found in reference texts such as the *CRC Handbook of Chemistry and Physics* (CRC Press).

The salts silver chloride (AgCl, $K_{sp}=1.77\times10^{-10}$) and silver iodide (AgI, $K_{sp}=8.51\times10^{-17}$) can be used to illustrate the principle of solubility driven ion exchange. The solubility products for these compounds are both fairly low, but $K_{sp}$ for silver iodide is lower by nearly 7 powers of ten, indicating that it is more insoluble than silver chloride. Thus, if solid silver chloride is placed in a solution containing iodide ions, the equilibrium lies on the side of the silver iodide, and the chloride ions will exchange with the iodide ions so that the more insoluble silver iodide is formed. On the other hand, if silver iodide is placed into a solution containing chloride ions, the ion exchange will not take place. In this manner, chloride ions in silver chloride coated on the surface of a substrate can be replaced by $^{125}I$ anions to form a radiation source of the present invention.

The metal salt layer which is the starting point for the above solution ion exchange process may be formed by a redox process such as that described above, or it may be applied directly by means of sputtering, vapor deposition, or other techniques known in the art. Alternatively, if a redox process described above is performed using an oxidizing solution containing a radioisotope, for example $H_3{}^{32}PO_4$, the radioisotope-containing metal salt layer may be obtained directly, eliminating the need for the ion exchange.

Another preferred method for making thin film sources of the present invention comprises oxidizing a metal, such as those bound to or incorporated in the substrate, and then binding an isotope to the metal oxide. The step in which the metal is oxidized preferably occurs spontaneously in air. Thus, metals such as aluminum and copper, which readily and spontaneously undergo oxidation to form their respective oxides, are preferred. Oxide formation occurs when the metal is exposed to air, but may be enhanced or increased by exposure to oxygen-enriched atmospheres or increased temperature. The binding of the isotope is preferably performed by immersing the metal oxide in a solution containing isotope ions, either simple or complex. The attraction between the metal oxide and the isotope ions is such that the isotope ions will bind to the metal oxide rather than existing free in solution. This binding or "plating" process may occur either with or without displacement of ions from the metal oxide.

There are several advantages to using the processes above to place active isotopes on a source as opposed to the ion implantation of radioisotopes and nuclear bombardment. One advantage is that unwanted isotopes are not formed. As discussed above with reference to Hehrlein '177, neutron activation of a metal-containing source produces numerous isotopes, making it very difficult to control the dose provided by the source.

Another advantage of the present method is that it does not create large quantities of radioactive waste. By using the correct quantity of radioisotope solution, very little waste is produced. Isotopes which are not incorporated into a given source remain in solution and may be used to form another source. Unlike radioactive ion implantation, there is no stray isotope-filled machine chamber that must be cleaned and safely discarded or taken out of use and allowed to "cool."

Yet another advantage of the present method is that it allows use of isotopes which cannot be readily obtained on a solid source by the other means known in the art. With the proper choice of materials and solutions and the disclosure herein, one skilled in the art would be able to create a reaction scheme to make a salt containing most any of the desirable therapeutic radioisotopes. Furthermore, by using particular long-lived isotopes, a radiation source with a longer half-life can be produced that is capable of delivering a dose with less variation between maximum and minimum. Use of an isotope with a longer half-life may provide for a radiation source which is capable of lowering the amount of radioactivity necessary to perform its function over that which incorporates a short-lived isotope.

Another advantage of the present invention is that the radioisotopes are held by strong atomic-level bonding interactions, and which are highly resistant to leaching or release under physiological conditions or during handling. Additionally, the use of ionic bonding is especially useful for radioisotope species such as iodine-125, as the salt form holds the normally volatile iodine atoms in place.

Another benefit to the solution processes of the present invention is that the density of activity of a given isotope or multiple isotopes may be controlled by simply controlling the time of immersion and/or the density and amount of metal salt or tie layer on the source.

Another advantage of the thin film source is that the structure lends itself to batch processing. The coating step can be done in relatively large volumes using common chemical attachment techniques found in the photographic film and semiconductor industries. Radioactive isotopes are commonly provided in solutions, so the final production step of adding the isotope may be as simple as soaking the coated substrate in the isotope solution. This can be simply performed in very small or very large sheet sizes. The ability to perform this step in small batches is advantageous because the amount of radiation in process can be adjusted to suit the radiation capabilities of the manufacturer.

The basic method, as discussed in part above, comprises providing a substrate and forming a coating comprising an insoluble metal salt with at least one radioactive isotope species thereon.

One preferred embodiment of thin film source of the present invention is that which has an isotope layer comprising the gamma-emitting isotope $^{125}I$. As mentioned previously, $^{125}I$ meets the criteria of an "ideal" isotope as defined by Amols and Jani. One method for making a thin film source having an isotope layer comprising $^{125}I$ is that which uses both solution methods discussed above. First, a substrate is provided that comprises silver or elemental silver is attached to the surface of the substrate using well-known methods such as ion implantation, vapor deposition, sputtering, electroplating, or rolling. The silver is then converted to silver chloride (AgCl) via an oxidation-reduction solution process such as that described above which uses an acidic solution of sodium chlorite to reduce the silver and produce silver chloride. Then the silver chloride-coated source is immersed in an ion exchange solution comprising sodium iodide in the form of $Na^{125}I$, wherein the AgCl is converted to $Ag^{125}I$ on the surface of the source. This manufacturing process may be performed quickly, easily and efficiently. In addition, the I-125 with a half-life of 60 days would provide an equivalent or lower dose of radiotherapy for a longer period of time.

As an alternative to the above method, silver chloride could be directly deposited to the surface of the thin film source by means of vapor deposition or other method known in the art, and then immersed in the ion exchange solution containing $Na^{125}I$.

In one specific embodiment of the present invention, a silver foil having a surface area of 4 $cm^2$ was immersed in a solution of 6M HCl and 1M $NaClO_2$ in a 10:1 ratio. A portion of the silver was thereby converted to silver chloride. The foil was then immersed in a bath having about 2 ml of a solution. The solution in the bath contained about 0.07% $Na^{125}I$ in NaI, and was prepared by dissolving 0.5 mg NaI in 2 ml water and adding 4.6 mCi $^{125}I$ into the solution. Following immersion, the resulting activity of the foil was measured at 2 mCi, which, when the amount of carrier (non-radioactive) iodine is factored in, corresponds to about $10^{18}$ atoms of iodine attached to the sheet. In a carrier free solution, this number of I-125 ions would result in an activity of 3 Ci per 4 $cm^2$ of substrate. This is 30,000 times the required activity for a 10 $\mu$Ci source.

Another preferred embodiment of thin film source of the present invention is that which has an isotope layer comprising 32P. A thin film source having an isotope layer comprising $^{32}P$ can be made by methods similar to that described above for $^{125}I$ using P-32 in the form of orthophosphoric acid ($H_3^{32}PO_4$) (New England Nuclear). First, a substrate is provided. The substrate may be manufactured to contain zinc or a zinc alloy, or the substrate may be coated with zinc or a zinc alloy by vapor deposition or other methods known in the art. The zinc is then converted to a salt such as zinc fluoride ($ZnF_2$, $K_{sp}=3.04\times10^{-2}$) via an oxidation-reduction process similar to that discussed above. The source is then activated by immersing the zinc fluoride-coated source in a solution containing phosphate ion in the form of $^{32}PO_4^{3-}$ or a soluble phosphate salt, whereby the more soluble fluoride ion is exchanged for phosphate to form zinc phosphate ($Zn_3(PO_4)_2$, $K_{sp}=5\times10^{-36}$).

Alternatively, the substrate may be directly coated with zinc fluoride or other similarly insoluble salt by vapor deposition or other means known in the art, and then placed in an ion exchange solution. Another alternative is to use a solution containing $H_3^{32}PO_4$ in the oxidation step so that the zinc is directly converted to zinc phosphate containing the radioisotope, thus eliminating the ion-exchange step. Yet another alternative is to deposit or form calcium fluoride ($CaF_2$, $K_{sp}=1.61\times10^{-10}$) and then expose this to a source of phosphate (orthophosphate) such as $H_3^{32}PO_4$ or $Na_3^{32}PO_4$.

There is an additional advantage to using zinc phosphate in the isotope layer. Zinc phosphate is a stable molecule and is often used in the automotive industry for paint adhesion to galvanized steel. Zinc phosphate has anticorrosive characteristics of its own, and has been used in the past to increase the corrosion resistance of steel. A zinc phosphate coating on a source made of steel, such as a wire or seed, may be an advantage to the source even in the case that it is not used as a radiation delivery device.

Yet another preferred embodiment of thin film source of the present invention is that which has an isotope layer comprising tungsten-188 (W-188 or $^{188}W$). Tungsten-188 undergoes beta decay to become rhenium-188 (Re-188 or $^{188}Re$). Rhenium-188 undergoes beta decay as well, but emits a much higher energy particle than in W-188 decay. The W-188 has a much longer half-life than does Re-188, thus the W-188 almost continuously creates more Re-188. This process is known as "generator," and these generator isotopes are referred to together by the shorthand W/Re-188 to indicate the relationship between the species. Generators are attractive for use in radiation delivery devices because they combine the energy levels of a short half-life species with the durability of the long half-life species. It is a general rule that particle energy and half-life are inversely proportional, and that long half-life species are more economical and practical to work with than short half-life species.

W/Re-188 is a beta emitting isotope with an energy about 10% higher than P-32. Where I-125 was discussed as a highly favorable gamma emitting isotope, W/Re-188 fits the criteria of both Amols and Jani for a highly favorable beta emitting species for IVRT. The advantage of the W/Re-188 source would be that the source would provide a dose which could be consistently administered over a long period of time. The half-life of W-188 is 70 days as compared to 14 days for the P-32. This represents a consistent dose rate as Re-188, itself a beta emitting isotope, is being produced by the decay of tungsten for a longer period of time.

Tungsten, in the form of tungstate ion ($WO_4^{2-}$) may be readily attached to an oxidized aluminum surface to produce a W/Re-188-containing thin film source of the present invention. An aluminum oxide surface may be attached to the source by sputtering $Al_2O_3$, or Al can be attached by implantation or deposition, followed by an oxidation step. Ambient environment will facilitate the formation of $Al_2O_3$ from aluminum which can be accelerated by increasing the temperature and/or using an oxygen-rich atmosphere. The aluminum oxide surface may then be immersed in a tungstate containing solution, such as an acidic solution of sodium tungstate ($Na_2^{188}WO_4$), in order to attach the W-188 to the alumina surface.

Tungsten may also be applied together with a phosphate in a manner similar to that disclosed by Larsen in U.S. Pat. No. 5,550,006, which is hereby incorporated into the present disclosure by this reference thereto. The method disclosed in Larsen is claimed for use in increasing adhesion of organic resists for printed circuits. The method was used to perform a phosphate conversion coating onto copper. This method may find its application in the radiation delivery device of the present invention in that many polymers and metals other than copper may be coated with this solution. In this method, phosphate may be in the form of $^{32}PO_4^{3-}$, tungsate may be in the form of $^{188}WO_4^{2-}$, or any combination of the isotopes in radioactive or stable form may be used.

Sources employing combinations of various isotopes provide another preferred embodiment in that beta-emitting isotopes may be combined with gamma-emitting isotopes where gamma isotopes can deliver dosage to greater depths.

Thin film sources comprising other metals, metal salts, and isotopes can be made by procedures similar or analogous to the preferred embodiments disclosed above, using materials appropriate for the chemistry of the isotope to be included, as can be determined by one skilled in the art in view of the disclosure herein.

In some embodiments of the thin film source of the present invention, it may be desirable to provide a tie layer, onto which the isotope layer will be placed. The tie layer may comprise adhesives, chemically activated surfaces, a chemical coating layer, or an organic or inorganic compound. Preferred tie layer materials include metals, alloys, metal salts, metal oxides, PVP, and other polymeric materials.

For some polymeric tie layers, the nature of the tie layer 14 will depend on the isotope to be attached. Many different coatings and attachment technologies are available, and new ones can be developed as applications are developed. For example, Iodine-125 (I-125) can be bound to the substrate by passing it over a substrate coated with a polyvinyl pyrolidone (PVP) as discussed previously. Other preferred polymeric-type tie layers comprise polymeric materials such as polyesters and polyimides.

Another preferred type of tie layer is the metal-type that which comprises a thin layer of metal, metal oxide, metal salt, or alloy. Depending upon the composition of the other layers and materials in the source, depositing a metal-type tie layer may allow an "alloying" process to take place between the metal of the tie layer and any metals present in the isotope layer. This may serve to enhance the tenacity of attachment of the metal salt, and hence the isotope. This may also occur if the tie layer comprises more than one metal or if more than one tie layer is used in making the source. Alloying of this type is common in the semiconductor industry, wherein a chromium layer is used as an initial layer in the deposition of gold. The chromium is alloyed with the gold in order to increase the strength at which the gold is bound to the substrate. If, for example, the isotope layer comprises a zinc salt, a metal such as copper or aluminum may be used as the tie layer. The tie layer may also be in the form of an oxide that provides oxygen to chemically bind the atoms of the metal salt layer thereby increasing the tenacity of attachment.

A metal-type layer to which the isotope layer is attached may comprise any suitable metal, metal oxide, metal salt or alloy. The layer may be deposited by vapor deposition, sputtering, ion plating, ion implantation, electrodeposition, or other method. When the tie layer is present, there may or may not be a clear distinction between the tie layer and the isotope layer. In performing its function, and depending on the chemistry of the materials involved, the tie layer may become blended, alloyed or intermingled with the isotope layer, thus blurring the lines between the layers. For many of the same reasons, the distinction between the tie layer and a metal-containing substrate layer may also be blurred. In these cases, the term tie layer is meant to be a functional or process-defining definition, rather than a reference to a physically distinct layer of the thin film source.

In another type of system that can be constructed, the tie layer 14 can incorporate a metal exchange surface, which will attach Pd-103 in the form of palladium metal drawn directly from solution. For example, the substrate layer, made from polyimide as disclosed previously, can be coated with reactive metals such as copper, aluminum, or chromium using commonly available techniques such as vapor deposition or sputtering. The coated substrate is then placed in a solution containing the isotope. The difference in oxidation-reduction (redox) potential between the coating metal and the isotope causes the isotope to deposit on the surface of the substrate film. This system can also be used to attach W-188 from a solution of tungsten salts or other metal salt isotopes as well.

Metal isotope species, such as Palladium-103 (Pd-103) or Tungsten/Rhenium-188 (W/Re-188) or Gd-153 can be attached by incorporating a chelating agent onto the polymer substrate, and then soaking the sheet in a solution of Palladium salts, Tungsten salts or Gadolinium salts. These types of chemical technologies can be incorporated into the source design described herein.

An experiment was done to test the effectiveness of using a copper tie layer to enhance the attachment of zinc fluoride onto a Mylar® sheet. A layer of $ZnF_2$ was placed on a first sheet of Mylar by vapor deposition. On a second sheet of Mylar, a layer of copper was placed by vapor deposition, followed by deposition of a layer of $ZnF_2$. The sheets were each placed into solutions of $H_3{}^{32}PO_4$ having similar activities and allowed to react for several hours. The P-32 activity was counted via scintillation counting. It was found that the sheet having the copper tie layer resulted in a greater adsorption of P-32: 71.6% for $Cu/ZnF_2$ vs. 56% for $ZnF_2$ after 1 hour; and 98.4% for $Cu/ZnF_2$ vs. 86% for $ZnF_2$ after 24 hours. Thus, after a significant period of time, the copper tie layer appears to promote and maintain adherence of the zinc salt to the Mylar surface, and can result in a source which has significantly more activity and adhesion than that without the copper tie layer.

Although the sources of the present invention may have isotopes which are sufficiently adherent without further treatment, in some embodiments of the present invention, it may be desirable to place an outer coating on the thin film source. An outer coating can provide further advantages for the thin film source of the present invention in that the coating can help provide additional means to bind the layers of the source together. Perhaps more importantly, an outer coating can increase the abrasion resistance of the source.

Sealed radioactive sources are those which have less than 5 nCi of removable activity. By providing a coating on the source which covers at least the isotope layer, the source can be protected from unwanted loss of activity due to mechanical abrasion of the surface of the source. This may be important, both for providing safe devices for the patient which leave radioisotopes behind only where they are desired, and for monitoring dosage to ensure that the dose which is to be provided by a source will actually reach the treatment site, and not be significantly diminished due to loss of isotope from abrasion which may occur during implantation. It also helps insure that, once the source is positioned for treatment, the radioisotopes will remain at that site and not be washed downstream.

Coating materials are preferably biocompatible, but not excessively biodegradable. Preferred materials include polymeric materials including cyanoacrylates (Loctite, Hartford, Conn.), acrylics, ethylene methyl acrylate (Exxon Chemical Co., Houston, Tex.), ethylene methyl acrylate/acrylic acid (EMA/AA) (Exxon Chemical Co., Houston, Tex.), urethanes and thermal plastic urethane (TPU) (BF Goodrich, Richfield, Ohio), PVDC, PBVC, PE, PET, and combinations thereof. Other preferred coatings may comprise other biocompatible materials, drugs or similar compounds, such as heparin. Many methods are available to perform the coating process, such as dip or immersion coating, spray coating, spin coating, gravure or shrink wrap tubing. If curing is required, the curing technique may be any of the various techniques available, such as air, heat, or UV. Preferably the thickness of the coating which is formed is 1 $\mu$m to 30 $\mu$m more preferably 10 $\mu$m to 20 $\mu$m.

One preferred embodiment of the present invention has a coating that is formed with cyanoacrylate. Another preferred coating layer is that formed by ethylene methyl acrylate/acrylic acid (EMA/AA) polymer. An aqueous dispersion of this coating material, preferably having a viscosity less than 100 centipoise, allows for use of any of the above-mentioned coating methods. UV curable polyurethane acrylate is also useful as a coating layer material. Yet another preferred coating layer is that formed by SARAN. Such a layer may be formed, for example, by immersing the source or a portion thereof into a melt of SARAN or a solution containing SARAN.

The coating layer may also be formed by a spin coating process. Spin coating the thin film source finds advantage in the flexibility to use coating materials having a wide range of viscosities. Low viscosity liquids may be spun on slowly, while a higher viscosity liquid may be spun at a higher velocity to maintain a thin coating. The substrate may be held in place by fixturing or by vacuum during the spin coating process. In an experiment, a dispersion of cyanoacrylate in acetone was dispensed on top of the metal salt surface while the substrate was rotated at 8000 rpm for five minutes. The resulting thickness of the coating was about 6.5 $\mu$m (0.00025 inch). When this specimen, having the spin-coated surface curable coating of cyanoacrylate was extracted in saline for 8 hours at 50° C., the amount of radioactivity extracted was negligible.

In another experiment, two sources were tested to demonstrate the effectiveness of the coating layer by measuring the amount of removable isotope on coated and uncoated sources. Both sources comprised a Mylar thin film substrate and a $ZnF_2/Zn_3(^{32}PO_4)_2$ isotope layer, with the coated source further comprising a cyanoacrylate coating layer made by dip coating an uncoated source. The test was performed on each source by wiping it with a cotton swab three times on each side. The activity of the swab was measured by scintillation counting. It was found that the amount of removable activity on the uncoated Mylar-based source was 6.76%, while on the coated source the removable activity was merely 0.050%.

In making some embodiments of the thin film source of the present invention, it may be desired that one or more portions of the source or substrate are not covered or coated by particular layers or portions of layers. In such embodiments, the source may be made by the use of masking techniques. In such a technique, the portions of the source or substrate which are to be left alone for a particular step or steps are covered with a piece of a material to serve as the mask. The other portions not covered by the mask are treated (reacted, coated) and then the mask is removed. For example, it may be preferred to have a small border of substrate surrounding the portion of the source onto which the isotope layer is placed. Such an arrangement may be preferred to reduce coating of the side surfaces of the substrate by the isotope layer, reduce edge effects or to enable several distinct and separate sources to be prepared on a single sheet of substrate having spaces therebetween which are not coated by isotope to that the individual sources may be separated once they are completely prepared without the risk of radioactive contamination of the blade or other implement which is used to cut or separate the individual sources.

In one embodiment, a plurality of sources comprising a Mylar substrate, alumina tie layer and $CaF_2/^{32}PO_4$ isotope layer are made using a mask. In this method, the Mylar sheet is placed between a plate and a mask. The plate may be formed of glass, metal or other suitable material. The mask is a stainless steel sheet from which several rectangular-shaped portions have been removed. The three pieces (plate, Mylar, mask) are secured together and then placed in a chamber. Alumina, which forms the tie layer, is then deposited on the rectangular-shaped portions of the Mylar which have been left exposed by the mask. Calcium fluoride is then deposited on the alumina. The mask is then removed, and the entire sheet placed in an ion-exchange bath containing $^{32}PO_4^{3-}$ ions to complete formation of the isotope layer. One or more outer coating layers may optionally be placed on the sheet prior to separation of the individual sources. The sources may also be coated individually following separation, such as following incorporation onto a balloon catheter.

The masking technique is described above in terms of making sources having a border of substrate surrounding an active area comprising a tie layer and isotope layer coating the substrate. Although described as such, the masking technique or variations thereof as would be apparent to one skilled in the art, may be used for other purposes in making the sources of the present invention, such as placing a coating layer on selected portions of the source, and placing different tie layers on different portions of the source.

Referring to FIG. 2, there is disclosed a radiation delivery catheter 18 incorporating the thin film source 10 in accordance with one aspect of the present invention. Although the description below is primarily directed to the radiation aspect of the invention, catheters embodying additional features known in the vascular dilatation art, such as carrying implantable stents, drug delivery, perfusion and dilatation features, or any combination of these features, can be used in combination with the balloon of the present invention as will be readily apparent to one of skill in the art in view of the disclosure herein.

The catheter 18 generally comprises an elongate tubular body 19 extending between a proximal control end 20 and a distal functional end 21. The length of the tubular body 19 depends upon the desired application. For example, lengths in the area of about 130 cm to about 150 cm are typical for use in radiation delivery by way of a femoral access following or during percutaneous transluminal coronary angioplasty.

The tubular body 19 may be produced in accordance with any of a variety of known techniques for manufacturing balloon-tipped catheter bodies, such as by extrusion of appropriate biocompatible plastic materials. Alternatively, at least a portion or all of the length of tubular body 19 may comprise a spring coil, solid walled hypodermic needle tubing, or braided reinforced wall, as is understood in the catheter and guide wire arts.

In general, tubular body 19, in accordance with the present invention, is provided with a generally circular exterior cross-sectional configuration having an external diameter with the range of from about 0.02 inches to about 0.065 inches. In accordance with one preferred embodiment of the invention, the tubular body 19 has an external diameter of about 0.042 inches (3.2 F) throughout most of its length for use in coronary applications. Alternatively, generally triangular or oval cross-sectional configurations can also be used, as well as other noncircular configurations, depending upon the number of lumen extending through the catheter, the method of manufacture and the intended use.

In a catheter intended for peripheral vascular applications, the tubular body 19 will typically have an outside diameter within the range of from about 0.039 inches to about 0.085 inches. Diameters outside of the preferred ranges may also be used, provided that the functional consequences of the diameter are acceptable for the intended purpose of the catheter. For example, the lower limit of the diameter for tubular body 19 in a given application will be a function of the number of fluid or other functional lumens, support structures and the like contained in the catheter, and the desired structural integrity.

In general, the dimensions of the catheter shaft and balloon can be optimized by persons of skill in the art in view of the present disclosure to suit any of a wide variety of applications. For example, the balloon of the present invention can be used to deliver radiation to large and small arteries and veins, as well as other lumens, potential spaces, hollow organs and surgically created pathways. The present inventor contemplates radiation delivery to the esophagus, trachea, urethra, ureters, fallopian tubes, intestines, colon, and any other location accessible by catheter which may benefit from radiation delivery. This includes surgically created lumens such as, for example, transjugular intrahepatic portosystemic shunts and others which will be recognized by those of skill in the art. Thus, although the present invention will be described herein primarily in terms of coronary artery applications, it is understood that this is for illustrative purposes only, and the present invention has much broader applicability in the field of radiation delivery.

Tubular body 19 must have sufficient structural integrity (e.g., "pushability") to permit the catheter to be advanced to a treatment site such as distal arterial locations without buckling or undesirable bending of the tubular body 19. Larger diameters generally have sufficient internal flow properties and structural integrity, but reduce perfusion in the artery in which the catheter is placed. Larger diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

As illustrated schematically in FIG. 2, the distal end 21 of catheter 18 is provided with at least one inflatable balloon 22. The proximal end 20 of catheter 18 is provided with a manifold 23 which may have one or more access ports, as is known in the art. Generally, manifold 23 is provided with a guide wire port 24 in an over the wire embodiment and a balloon inflation port 25. Additional access ports are provided as needed, depending upon the functional capabilities of the catheter 18.

The balloon 22 can also be mounted on a rapid exchange type catheter, in which the proximal guidewire port 24 would not appear on the manifold 23 as is understood in the art. In a rapid exchange embodiment, the proximal guidewire access port 24 is positioned along the length of the tubular body 19, such as between about 1 and about 20 cm from the distal end of the catheter.

Referring to the embodiment of the balloon illustrated in FIG. 2, a focal or enlarged zone 32 is positioned between a proximal reference zone 28 and a distal reference zone 30. The relative lengths of each of the three zones may vary considerably depending upon the intended use of the balloon. In general, suitable dimensions of the balloon, both in terms of diameters and lengths, as well as other catheter dimensions, are disclosed in U.S. Pat. No. 5,470,313 to Crocker, et al., entitled Variable Diameter Balloon Dilatation Catheter, the disclosure of which is incorporated in its entirety herein by reference.

In one particular application, the central zone 32 has an axial length of about 25 mm, and each of the proximal zone 28 and distal zone 30 have an axial length of about 5 mm. At an inflation pressure of about 8 atmospheres, the proximal zone 28 has an outside diameter of about 3 mm, and the central zone 32 has an outside diameter of about 3.4 mm. The same balloon at 18 atmospheres inflation pressure has an outside diameter of about 3.1 mm in the proximal zone 28 and an outside diameter of about 3.5 mm in the central zone 32. That particular balloon was constructed from PET, having a wall thickness of about 0.0006 to about 0.0008 inches.

In accordance with an alternative embodiment of the balloon of the present invention, illustrated in FIG. 3, the balloon 26 has a generally cylindrical inflated profile throughout its axial working length such as with conventional PTCA balloons. Either the stepped balloon of FIG. 2 or the cylindrical balloon of FIG. 3 can be readily provided with the radiation source 10 discussed below in accordance with the present invention.

The overall dimensions of any particular balloon 22 or 26 will be governed by the intended use, as will be well understood to those of ordinary skill in the art. For example, balloons can be inflatable to a diameter of anywhere within the range of from about 1.5 mm to about 10 mm. For coronary vascular applications, the central zone 32 or overall balloon 26 will normally be inflatable to a diameter within the range of from about 1.5 mm to about 4 mm, with balloons available at about every 0.25 mm increment in between.

The proximal zone 28 and distal zone 30 are generally inflatable to a diameter within the range of from about 1.25 mm to about 9.5 mm. For coronary vascular applications, the proximal and distal zones 28, 30 are preferably inflatable to a diameter within the range of from about 1.25 mm to about 3.5 mm.

The axial length of the central section 32 can be varied considerably, depending upon the desired radiation delivery length as will become apparent. For example, the axial length of the central section 32 may be anywhere within the range of from about 0.5 cm to about 5.0 cm or longer. For coronary vascular applications, the axial length of the central section 32 will normally be within the range of from about 0.5 cm to about 2.0 cm, if the balloon is designed to deliver radiation as well as simultaneously perform conventional PTCA. In a radiation delivery balloon which is not intended to perform PTCA, the axial length of the central zone 32 may exceed the typical length of the lesion, and, in coronary vascular applications, the axial length may be within the range of from about 0.5 cm to about 5 cm or longer.

The axial length of the proximal zone 28 and distal zone 30 may also be varied considerably, depending upon the desired performance characteristics. In general, axial lengths of the cylindrical portion of the proximal zone 28 and distal zone 30 of at least about 3 mm appear useful.

Referring to FIG. 4, there is disclosed a radioactive balloon in accordance with the present invention, configured as in FIG. 3. The balloon 26 comprises a radiation delivery zone 32. The radiation zone 32 comprises an inner balloon wall 36 surrounded by the radiation source 10. Preferably, the radiation source 10 is surrounded by an outer sleeve 38. In the illustrated embodiment, the radiation source 10 is entrapped between the outer sleeve 38 and balloon wall 36, and the outer sleeve 38 is adhered to the balloon wall 36 or catheter shaft such as through the use of thermal bonding or an adhesive. Suitable adhesives include medical grade UV curable and urethane adhesives known in the art. Any of a wide variety of alternate techniques known to those of skill in the art can also be utilized for securing an outer sleeve 38 to the balloon, such as fusing, heat shrinking, spot welding, and the like.

The sleeve 38 may extend only slightly longer in the axial direction than the axial length of the radiation source 10. The outer sleeve 38 can alternatively extend the entire length of the balloon, or longer, such that it is necked down at the proximal end of the balloon to the catheter shaft and similarly necked down at the distal end of the balloon to the catheter shaft. One suitable outer sleeve 38 comprises 0.0003 inch wall thickness PET tube. Other materials could be polyolefins, nylons, or urethanes, or compounds thereof. Alternatively, the outer sleeve 38 can be omitted, so long as the radiation source 10 is adequately secured to the balloon.

The balloon 26 is mounted on a tubular body 19, which preferably comprises at least a guidewire lumen 40 and an inflation lumen 42. In the illustrated embodiment, the two lumens 40 and 42 are illustrated in a concentric relationship as is known in the art. Alternatively, the two lumens 40 and 42 can be formed in a side-by-side geometry, (FIG. 5) such as through the use of conventional extrusion techniques.

Referring to FIG. 5, there is illustrated a perfusion embodiment of the present invention. The radiation delivery catheter with perfusion 50 comprises an elongate flexible tubular body 52 having a distal balloon 54 thereon. In this embodiment the tubular body 52 is preferably configured in a side by side orientation, as is well understood in the catheter art. Thus, the tubular body 52 comprises at least an inflation lumen 56 and a guidewire lumen 58. Additional lumen may be provided, depending upon the desired functionality of the catheter.

The guidewire lumen 58 extends from the proximal guidewire access port (not illustrated) to the distal guidewire access port 66 as is well known in the art. The proximal guidewire access port may either be on the side wall of the catheter as has been discussed in a rapid exchange embodiment, or at the proximal manifold in an over the wire embodiment. A perfusion section 60 of the guidewire lumen 58 extends through the balloon 54, and places a plurality of proximal ports 62 in fluid communication with a plurality of distal ports 64. In this manner, the guidewire (not illustrated) can be proximally retracted within the guidewire lumen 58 to a position proximal to the proximal ports 62 once the balloon 54 has been positioned at the treatment site. The balloon 54 can be inflated by injecting inflation media through the inflation lumen 56, and the perfusion section 60 permits blood to perfuse across the balloon by way of proximal ports 62 and distal ports 64.

As discussed elsewhere herein, the balloon 54 is provided with a thin film source 10 which may comprise one or more layers of radioactive thin film source. The thin film source 10 may be adhered to the inside surface or outside surface of the balloon wall and may be further entrapped within an outer tubular layer 70 as illustrated. Alternatively, the thin film source 10 is adhered to the inside surface or outside surface of the balloon wall without an outer layer 70. Tubular layer 70 preferably is positioned concentrically about the thin film source 10 and heated or bonded to attach to the balloon. The axial length of the thin film source 10 on, for example, a 3 cm long balloon, may be anywhere within the range of from about 15 mm to about 27 mm measured along the axis of the catheter.

In any of the foregoing embodiments, the isotope layer 16 may comprise either a homogenous isotope population, or a blend of two or more isotopes. For example, a blend may be desirable to achieve a desired combination of half life, activity, penetration or other characteristics in the finished product. Two or three or four or five or more different isotopes may be dispersed uniformly throughout the isotope layer 16, or may be concentrated in different zones along the isotope layer, depending upon the desired activity profile in the finished thin film radiation source.

In accordance with another aspect of the present invention, the thin film radiation source is applied to a delivery structure such as a balloon in a manner that permits radially asymmetric delivery. This may be desirable for treating only a selected site within the circumference of the arterial wall, such as in the case of an eccentric stenosis.

In this embodiment radioisotope is provided only along a portion of the circumference of the delivery structure such as a balloon. The radioisotope zone may comprise anywhere in the range of from about 10% to about 70% of the total circumference of the balloon, and, in one embodiment, is within the range of from about 30% to about 50% of the total circumference of the balloon. This may be accomplished in any a variety of manners, such as masking the thin film prior to application of the isotope, applying a blocking layer to block release of radiation from portions of the circumference, and the like as will be apparent to those of skill in the art in view of the disclosure herein. In one embodiment, a thin film sheet is prepared as has been described herein, except that radioisotope is only adhered to the thin film substrate in a series of discrete zones which are separated by nonradioactive portions of substrate. The radioactive zones can be spaced apart along the substrate sheet to correspond to the circumference of the delivery balloon, so that when the radioactive thin film is wrapped around the balloon, the radioactive zones align with each other to provide a radioactive stack on only a predetermined circumferential portion of the balloon.

Thus, at least a first and a second zone can be provided on the thin film source in accordance with the present invention. In one embodiment the first zone is radioactive and the second zone is not radioactive. In another embodiment, the first zone has a first radioactive activity and the second zone has a second, lesser radioactive activity. Alternatively, other characteristics of the radioactive source can be varied between the first zone and the second zone, depending upon the desired delivery performance.

In accordance with another aspect of the present invention, balloon catheter may be constructed which allows for delivery of radiation to differing sizes of lumens. In such a device, the balloon preferably comprises a compliant plastic material. The substrate for the source may be either the balloon itself or another thin film of a compliant or elastomeric plastic. As the pressure inside the compliant balloon is increased, the outer diameter of the balloon will increase. Thus, a single balloon catheter may be used to treat different size lumens by simply varying the pressure and hence the inflation diameter of the balloon.

The increase in diameter will result in a decrease in density of isotope atoms per surface area. By adjusting the dwell time, the predetermined dosage can be delivered. For example, a 20 mm balloon having an outer diameter of 2.0 mm and $10^{17}$ atoms of isotope on the surface will result in a density of $7.96 \times 10^{14}$ atoms/mm$^2$. If this balloon were pressurized to increase to a 2.5 mm diameter, the density would decrease to $6.34 \times 10^{14}$ atoms/mm$^2$. This is a 20% decrease, resulting in a need for a 20% increase in dwell time to achieve an equivalent dose. There.may also be a slight decrease in balloon length with increased diameter of inflation. This change, however, is dependent on the level of compliance and may be negligible in most cases, but is easily remedied by careful selection of balloon size.

In accordance with the method of the present invention, a balloon catheter such as any described above is percutaneously inserted and transluminally advanced through a patient's vasculature, to the treatment site. At the treatment site, the balloon is expanded to position the radioactive delivery layer against the vessel wall. The balloon remains expanded for a sufficient radiation delivery time, and is thereafter deflated and withdrawn from the patient. The balloon may be introduced through an introduction sheath, which can be proximally withdrawn to expose the balloon once the balloon has been positioned at the treatment site.

If delivery times greatly in excess of one or two minutes are clinically desirable, the catheter 18 may be provided with a perfusion conduit such as that illustrated in FIG. 5. Any of a variety of perfusion structures can be utilized, such as any of those disclosed in U.S. Pat. No. 5,344,402 to Crocker entitled Low Profile Perfusion Catheter or U.S. Pat. No. 5,421,826 to Crocker et al. entitled Drug Delivery and Dilatation Catheter Having a Reinforced Perfusion Lumen, the disclosure of each of which is incorporated in its entirety herein by reference.

In accordance with another aspect of the method of the present invention, the radiation delivery and balloon dilatation catheter of the present invention is utilized to simultaneously dilate a stenosis in a vessel and deliver a treating dose of radiation. The catheter is percutaneously introduced and transluminally advanced through the arterial system to reach a stenosis. The balloon is positioned within the stenosis, and inflated to expand the stenosis as is known in the art. During the expansion step, the balloon is delivering a treatment dose of radiation to the vessel wall. The balloon may then be left in position in the inflated profile optionally with perfusion for a sufficient period of time to deliver the desired dose of radiation. The balloon is thereafter deflated, and the catheter is withdrawn from the treatment site.

In accordance with a further aspect of the method of the present invention, the radiation delivery catheter of the present invention may be utilized to simultaneously implant a stent while delivering a dose of radiation. In accordance with this aspect of the method, a stent is positioned on the radiation delivery balloon prior to percutaneous insertion within the patient. The balloon carrying a stent thereon is thereafter percutaneously inserted and transluminally advanced through the patient's vasculature to the treatment site. The balloon is expanded at the treatment site to expand the stent, while simultaneously delivering a dose of radiation. The balloon is thereafter deflated, and withdrawn from the patient, leaving the expanded stent in position at the site.

In accordance with another aspect of the present invention, there is provided a method of treating a previously implanted stent or graft with exposure to a dose of radiation. The method comprises the steps of identifying a previously implanted stent or graft within a body lumen. A radiation delivery catheter of the type described elsewhere herein is positioned within the stent or graft, and the balloon is inflated to position the radioactive source against or near the interior wall of the stent or graft. The balloon may either be inflated to a sufficient pressure to further dilate the stent or graft, or inflated sufficiently to position the radiation source against the interior wall of the stent or graft without additional stent or graft expansion or sizing. Following delivery of a dose of radiation, the balloon is deflated and removed from the patient.

Any of the foregoing methods may be accomplished either with or without the perfusion capability disclosed elsewhere herein. In addition, any of the foregoing methods may be accomplished through the use of an over the wire embodiment of the invention or a rapid exchange embodiment of the invention as has been disclosed elsewhere herein.

Thus, in accordance with the present invention, there is provided a catheter having a radiation delivery layer on the balloon, which permits a relatively low energy thin film source to be positioned directly against, or within about 0.001 inches and preferably no more than about 0.003 inches from the vascular wall, depending upon the thickness of any outer sleeve 38 or 70 or other coating. In addition, the present configuration expels substantially all blood or other fluids from between the radiation source and the vessel wall, throughout the entire interior circumference of the vessel for the axial length of the balloon. As a consequence, the radiation is not required to penetrate multiple structures as well as blood within the vessel in order to reach the vessel wall. In addition, radiation delivery is essentially uniform throughout the entire circumference of the vessel at the delivery site.

The configuration of the balloon of the present invention is such that the radiation delivery layer does not need to be elastic and can simply be folded with the balloon material into the reduced, insertion profile. Higher radiation dosages than those specifically described herein can be readily achieved, such as through the use of longer dose times and/or higher activity isotopes and/or higher density of the isotope layer and/or more layers of the thin film source.

Although the present invention has been described in terms of certain preferred embodiments, other embodiments of the invention will become apparent to those of skill in the art in view of the disclosure herein. Accordingly, the scope of the present invention is not intended to be limited by the foregoing, but rather by reference to the attached claims.

What is claimed is:

1. A method of treating a site within a vessel, comprising:
identifying a site in a vessel to be treated;
providing a radiation delivery catheter including an elongate flexible tubular body having an expandable balloon with a thin film radiation delivery layer thereon, said thin film comprising a substrate layer and an isotope layer comprising a metal salt or a metal oxide, and at least one radioactive isotope;
positioning the balloon within the treatment site;
inflating the balloon within the treatment site;
delivering a circumferentially substantially uniform dose of radiation from the delivery balloon to the treatment site;
deflating the balloon; and
removing the balloon with the thin film radiation delivery layer thereon from the treatment site.

2. A method of treating a site within a vessel as in claim 1, wherein said site comprises a previously implanted prosthesis, and positioning the balloon comprises positioning the balloon within the prosthesis.

3. A method of treating a site within a vessel as in claim 2, wherein the prosthesis comprises a stent or graft.

4. A method of treating a site within a vessel as in claim 1, wherein said isotope is a gamma or beta emitting isotope.

5. A method of treating a site within a vessel as in claim 1, wherein the radioactive isotope comprises an isotope selected from the group consisting of P-32, I-125, Pd-103, W/Re-188, As-73, and Gd-153.

6. A method of treating a site within a vessel as in claim 1, wherein the radiation delivery layer further comprises a tie layer disposed between the support layer and the isotope layer.

7. A method of treating a site within a vessel as in claim 1, wherein the radiation delivery layer further comprises a coating layer upon the isotope layer.

8. A method of treating a site within a vessel as in claim 7, wherein said coating layer comprises a material selected from the group consisting of cyanoacrylates, acrylics, acrylates, acrylic acid, urethanes, polybutyl vinyl chloride, and polyvinylidine chloride.

9. A method of treating a site within a vessel as in claim 1, further comprising perfusing blood from a proximal side of the balloon to a distal side of the balloon while the balloon is inflated.

10. A method of treating a site within a vessel as in claim 1, wherein the catheter further comprises a proximal guide wire access port on the tubular body, positioned distally of the proximal end of the tubular body.

11. A method of delivering a dose of radiation to a lumen, comprising:

providing a radiation delivery catheter including an elongate flexible tubular body having a radiation delivery layer carried by an expandable support on the tubular body, said radiation delivery layer comprising a substrate layer and an isotope layer comprising a metal salt or a metal oxide, and at least one radioactive isotope;

positioning the expandable support within the lumen;

radially expanding the support within the lumen;

delivering a circumferentially substantially uniform dose of radiation to the lumen in the region of the radiation delivery layer;

radially contracting the support; and removing the support and the radiation delivery layer from the lumen.

12. A method as in claim 11, wherein radially expanding the support comprises inflating an inflatable balloon.

13. A method as in claim 11, further comprising perfusing blood from a proximal side of the expandable support to a distal side of the expandable support while the support is expanded.

14. A method of treating a site within a vessel as in claim 11, wherein said isotope is a gamma or beta emitting isotope.

15. A method as in claim 11, wherein the radioactive isotope comprises an isotope selected from the group consisting of P-32, I-125, Pd-103, W/Re-188, As-73, and Gd-153.

16. A method as in claim 11, wherein the radiation delivery layer further comprises a tie layer disposed between the support layer and the isotope layer.

17. A method as in claim 11, wherein the radiation delivery layer further comprises a coating layer upon the isotope layer.

18. A method as in claim 17, wherein said coating layer comprises a material selected from the group consisting of cyanoacrylates, acrylics, acrylates, acrylic acid, urethanes, polybutyl vinyl chloride, and polyvinylidine chloride.

19. A method as in claim 11, wherein the catheter further comprises a proximal guide wire access port on the tubular body, positioned distally of the proximal end of the tubular body.

20. A method as in claim 11, wherein the substrate layer is integral with the support.

21. A method as in claim 11, wherein the substrate layer is layered upon the support.

22. A method as in claim 11, wherein positioning the support comprises positioning the isotope layer within a stent.

23. A method as in claim 11, wherein the lumen is selected from the group consisting of large and small arteries, large and small veins, hollow organs, surgically created pathways, esophagus, trachea, urethra, ureters, fallopian tubes, intestines and colon.

24. A method of simultaneously performing balloon dilatation of a stenosis in a body lumen and delivering radiation to the body lumen, comprising:

identifying a stenosis in a body lumen;

providing a treatment catheter having an elongate flexible tubular body having an expandable balloon with a thin film radiation delivery layer thereon, said thin film comprising a substrate layer and an isotope layer comprising a metal salt or a metal oxide, and at least one radioactive isotope;

percutaneously inserting and transluminally advancing the balloon through the vessel;

positioning the balloon within the stenosis;

inflating the balloon to radially expand the vessel in the area of the stenosis;

simultaneously delivering radiation from the thin film to the vessel wall; and removing the balloon with the radiation delivery layer thereon from the stenosis.

25. A method of simultaneously delivering a stent and radiation to a treatment site in body lumen, comprising:

identifying a treatment site in a body lumen;

providing a treatment catheter having an elongate flexible tubular body having a radially expandable support with a thin film radiation delivery layer thereon and an expandable stent carried by the expandable support, said thin film comprising a substrate layer and an isotope layer comprising a metal salt or a metal oxide, and at least one radioactive isotope;

positioning the support at the treatment site in the lumen;

radially expanding the support to expand and deliver the stent;

simultaneously delivering radiation from the thin film to the lumen wall; and removing the support and thin film from the treatment site.

* * * * *